(12) United States Patent
Balestra et al.

(10) Patent No.: US 10,131,642 B1
(45) Date of Patent: Nov. 20, 2018

(54) ALDOSTERONE SYNTHASE INHIBITORS

(71) Applicant: Boehringer Ingelheim International GmbH, Ingelheim am Rhein (DE)

(72) Inventors: Michael Balestra, New Fairfield, CT (US); Jörg M. Bentzien, White Plains, NY (US); Jennifer Burke, Newtown, CT (US); Derek Cogan, Ridgefield, CT (US); Xin Guo, Danbury, CT (US); Keith R. Hornberger, Southbury, CT (US); John Lord, Poughkeepsie, NY (US); Kenneth M. Meyers, Seymour, CT (US); Zhaoming Xiong, Ridgefield, CT (US); Maolin Yu, Brookfield, CT (US); Zhonghua Zhang, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/545,331

(22) PCT Filed: Jan. 28, 2016

(86) PCT No.: PCT/US2016/015251
§ 371 (c)(1),
(2) Date: Jul. 21, 2017

(87) PCT Pub. No.: WO2016/123275
PCT Pub. Date: Aug. 4, 2016

Related U.S. Application Data

(60) Provisional application No. 62/109,890, filed on Jan. 30, 2015.

(51) Int. Cl.
| A61P 13/12 | (2006.01) |
| --- | --- |
| C07D 261/20 | (2006.01) |
| C07D 413/04 | (2006.01) |
| C07D 413/06 | (2006.01) |
| C07D 413/10 | (2006.01) |
| C07D 413/12 | (2006.01) |
| C07D 498/04 | (2006.01) |

(52) U.S. Cl.
CPC .......... *C07D 261/20* (2013.01); *A61P 13/12* (2018.01); *C07D 413/04* (2013.01); *C07D 413/06* (2013.01); *C07D 413/10* (2013.01); *C07D 413/12* (2013.01); *C07D 498/04* (2013.01)

(58) Field of Classification Search
CPC .... C07D 261/20; C07D 13/06; C07D 498/04; C07D 413/12; C07D 413/04; C07D 413/10; A61P 13/12
See application file for complete search history.

(56) References Cited

U.S. PATENT DOCUMENTS

| 7,342,036 B2 * | 3/2008 | Suzuki | ................. C07D 261/20 514/379 |
| --- | --- | --- | --- |
| 2010/0069451 A1 * | 3/2010 | Neggiani | ............. C07D 261/20 514/379 |

OTHER PUBLICATIONS

Chemical Abstract Service STN Registry Database [online] RN 727666-40-2 [Entered STN: Aug. 17, 2004]. (Year: 2004).*
Chemical Abstract Service STN Registry Database [online] RN 696631-26-2 [Entered STN: Jun. 21, 2004]. (Year: 2004).*

* cited by examiner

*Primary Examiner* — Amanda L Aguirre
(74) *Attorney, Agent, or Firm* — Paula K. Wittmayer; David L. Kershner

(57) ABSTRACT

The present invention relates to compounds of formula I: and pharmaceutically acceptable salts thereof, wherein X, $R^1$, $R^2$ and $R^3$ are as defined herein. The invention also relates to pharmaceutical compositions comprising these compounds, methods of using these compounds in the treatment of various diseases and disorders, processes for preparing these compounds and intermediates useful in these processes.

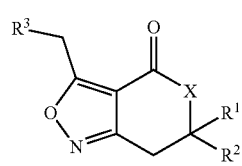

I

11 Claims, No Drawings

ALDOSTERONE SYNTHASE INHIBITORS

FIELD OF THE INVENTION

This invention relates to heteroaryl compounds that are useful as inhibitors of aldosterone synthase (CYP11B2) and are thus useful for treating a variety of diseases that are mediated or sustained by aldosterone activity, including renal disease, diabetic nephropathy, cardiovascular diseases and fibrotic disorders. This invention also relates to pharmaceutical compositions comprising these compounds, methods of using these compounds in the treatment of various diseases and disorders, processes for preparing these compounds and intermediates useful in these processes.

BACKGROUND

Aldosterone is a steroid hormone having mineralocorticoid activity. It is produced primarily by the adrenal glomerulosa in response to angiotensin II, adrenocorticotropic hormone and increased serum potassium levels. A primary physiological role of aldosterone in the kidney is to maintain sodium and potassium balance by regulating cation exchange ($Na^+$ reabsorption and $K^+$ secretion) in the distal nephron. However, aldosterone has also been shown to be a pro-inflammatory and pro-fibrotic hormone in blood vessels, heart and kidneys. The effects of aldosterone on gene expression are mediated via binding to the mineralocorticoid receptor (MR) and a canonical nuclear hormone receptor pathway. However, the hormone also elicits rapid, non-genomic responses, including acute regulation of the activity of tubular ion transporters, for example $Na+/H^+$ exchangers (NHEs), $H^+$-ATPase, ENaC, and $Na^+/K^+$ ATPase (D. W. Good, 2007, Hypertension, 49, 728-739). It is likely that some of these effects are mediated by MR-independent pathways. Conversely, the MR can bind alternative ligands, including deoxycorticosterone, corticosterone, cortisol and progesterone. Thus, inhibition of aldosterone synthesis is predicted to have a pharmacodynamic profile distinct from what is observed with MR antagonists.

Aldosterone is synthesized in the zona glomerulosa of the adrenal glands, where a single enzyme, CYP11B2 (aldosterone synthase), catalyzes the 3-step conversion of 11-deoxycorticosterone (11-DOC) to aldosterone, via corticosterone and 18-hydroxycorticosterone. Adrenal aldosterone synthase activity is regulated by Angiotensin II and K+ levels and unidentified adipocyte-derived mediators. Low levels of aldosterone synthase have also been detected in the heart and CNS, though the physiological relevance is uncertain, perhaps relating to paracrine effects. Systemic aldosterone is believed to derive essentially entirely from the adrenals.

Beyond its role in regulating sodium and potassium balance, aldosterone has been shown to have pro-inflammatory and pro-fibrotic actions in multiple tissues including the kidney, blood vessels and the heart. The harmful effects of inappropriate aldosterone levels on blood pressure and cardiac, renal, cerebral and vascular function and structure, have been widely reported in the literature, including: i) increase in sodium retention through $Na^+/K^+$ ATPase pump induction in distal tubules resulting in volume expansion and high blood pressure, ii) endothelial dysfunction, iii) oxidative stress, iv) renal and cardiac hypertrophy, v) fibroblast proliferation, and, vi) excessive synthesis of extracellular matrix resulting in renal, cardiac and vascular fibrosis.

Benefits of aldosterone blockade/inhibition include reduction of kidney fibrosis and improvement of glomerular filtration rate and albuminuria in models of chronic kidney disease (CKD) and diabetic nephropathy. This is supported by pre-clinical data (for example, Fiebler et al., 2005, Circulation, 111, 3087-3094; Lea et al., 2009, Kidney International, 75, 936-945). Other benefits reported in the literature include decreased blood pressure and end-organ damage (heart, kidney, vessels) in both renin-dependent and salt-sensitive hypertension.

Although many of aldosterone's known effects are mediated through mineralocorticoid receptor (MR) activation, and much of the evidence favoring targeting this pathway comes from experiments with MR antagonists, non MR-mediated effects are reported and knockout mice for MR and aldosterone synthase exhibit different phenotypes (Makhanova et al. 2006, Berger et al. 1998, Funder 2007). These observations further suggest that aldosterone synthase inhibitors may have a different profile and offer advantages compared to MR antagonists.

For example, several aldosterone actions are not inhibited by MR antagonists, including the potentially deleterious effects on the vasculature (increased peripheral vascular resistance), the heart (effects on myocardial re-polarization) and the endocrine system (decreased insulin secretion). Furthermore, MR antagonism leads to an increase in circulating aldosterone, predicted to increase aldosterone signaling via non-MR pathways and, potentially, partially overcoming the MR blockade itself.

Current therapeutic strategies focus on slowing progression and treating conditions underlying diabetic nephropathy: control of blood glucose and control of high blood pressure. Angiotensin converting enzyme (ACE) inhibitors and angiotensin receptor blockers (ARB) have shown renal benefit in diabetic patients. To date, representatives of the ACE inhibitor class and from the ARB class have been approved for the treatment of diabetic nephropathy. These therapies represent limited benefit for the diabetic nephropathy patients.

Although the use of ACE inhibitors and ARBs represents the current standard of care for patients with diabetic nephropathy, patients progressively lose kidney function while on these medications, as seen in the IDNT (E. J. Lewis et al., 2001, N. Engl. J. Med., 345, 851-860) and RENAAL (B. M. Brenner et al., 2001, N. Engl. J. Med., 345, 861-869) studies, which reported a decrease over time in estimated glomerular filtration rate, which is an accurate measure of chronic kidney disease progression in patients treated by these conventional methods. At stage 5 chronic kidney disease, renal replacement therapy is required, in the form of either dialysis or transplant.

Aldosterone synthase inhibition may also be predicted to offer advantages as add-on therapy with ACE inhibitors and ARBs. Notably, 25-50% of patients receiving these agents experience "aldosterone breakthrough" in which aldosterone levels initially lowered by these treatments eventually return to pretreatment levels. This phenomenon would not occur with direct aldosterone synthase inhibition and could enhance efficacy in combination therapy.

There remains a high unmet medical need to treat diabetic nephropathy, to halt or regress disease progression by specifically targeting the underlying pathophysiological mechanisms associated with chronic inflammation and fibrosis, irrespective of the original cause of the disease and when co-administered with current therapies. The studies described above and in the literature provide evidence that inhibitors of aldosterone synthesis will be useful for the treatment of diabetic kidney disease including diabetic nephropathy; non-diabetic kidney disease including glomerulosclerosis, glomerulonephritis, IGA nephropathy, nephritic syndrome and focal segmental glomerulosclerosis (FSGS); cardiovascular diseases including hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism; adrenal hyperplasia and primary and secondary hyperaldosteronism.

BRIEF SUMMARY OF THE INVENTION

The present invention provides novel compounds that inhibit aldosterone synthase and thus useful for treating a variety of diseases and disorders that can be alleviated by lowering levels of aldosterone including renal disease, diabetic nephropathy, cardiovascular diseases and fibrotic disorders. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In an embodiment of the invention, there are provided compounds of the formula I

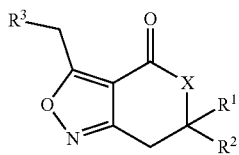

I wherein:
X is —CH$_2$— or —O—;
R$^1$ and R$^2$ are independently selected from H, C$_{1-3}$alkyl, —CH$_2$-cyclopropyl, benzyl, and tetrahydropyran-4-yl, provided that R$^1$ and R$^2$ are not both H; or
R$^1$ and R$^2$ may together form a spiro cyclobutyl ring;
R$^3$ is selected from
phenyl, optionally substituted with one to two groups independently selected from the group G, consisting of
—SO$_2$C$_{1-3}$alkyl, —CN, -halogen, —C(O)OH, —C(O)NR$^4$R$^5$, —O(CH$_2$)$_{2-3}$C(O)N(R$^6$)(R$^7$), —O(CH$_2$)$_2$S(O)(NH)CH$_3$, and —O(CH$_2$)$_{2-3}$SO$_2$CH$_3$;
wherein if R$^1$ and R$^2$ are both independently of each other selected from H and C$_{1-3}$alkyl, the phenyl is substituted with one to two groups selected from the group G; and wherein
if the phenyl is substituted with at least one of the substituents listed in group G, or if R$^1$ and/or R$^2$ is a group other than H or C$_{1-3}$alkyl, or if X is O, the phenyl may also be optionally substituted with C$_{1-3}$alkyl, or —OC$_{1-3}$alkyl;
cyclopropyl;
2,3-dihydro-benzo[1,4]dioxin-6-yl;
4H-benzo[1,4]oxazin-3-on-6-yl;
tetrahydropyran-4-yl;
piperidin-4-yl, optionally substituted with a group selected from —C(O)CH$_3$, —C(O)CH$_2$OCH$_3$, —C(O)CH$_2$OH, —C(O)CH$_2$SO$_2$CH$_3$ and —C(O)NH$_2$;
pyridyl, optionally substituted with —OCH$_3$;

R$^4$ and R$^5$ are independently selected from H and C$_{1-3}$alkyl, wherein the C$_{1-3}$alkyl is optionally substituted with one to two groups independently selected from —SO$_2$CH$_3$, —SO$_2$NH$_2$, OH, —OCH$_3$, —CN and a spiro C$_{3-5}$cycloalkyl group; or
R$^4$ and R$^5$ together with the N they are attached to may form a pyrrolidine, piperidine or piperazine ring, optionally substituted with one to two groups independently selected from —OH, —SO$_2$CH$_3$, —CH$_3$ and oxo;
R$^6$ and R$^7$ are independently selected from H and CH$_3$; or together with the N they are attached to may form a pyrrolidine ring, optionally substituted with —OH;
and the pharmaceutically acceptable salts thereof.
In another embodiment, there are provided compounds of the formula I as described according to the first embodiment, wherein
R$^1$ and R$^2$ are independently selected from H, C$_{1-3}$alkyl and —CH$_2$-cyclopropyl, provided that R$^1$ and R$^2$ are not both H; or
R$^1$ and R$^2$ may together form a spiro cyclobutyl ring;
R$^3$ is selected from
phenyl, substituted with one to two groups independently selected from —SO$_2$CH$_3$, —CN, —F, —I, —C(O)NR$^4$R$^5$, —O(CH$_2$)$_{2-3}$C(O)N(R$^6$)(R$^7$), —O(CH$_2$)$_2$S(O)(NH)CH$_3$, and —O(CH$_2$)$_{2-3}$SO$_2$CH$_3$; and
piperidin-4-yl, substituted on the nitrogen with a group selected from —C(O)CH$_3$, —C(O)CH$_2$OCH$_3$, —C(O)CH$_2$OH, —C(O)CH$_2$SO$_2$CH$_3$ and —C(O)NH$_2$;
R$^4$ and R$^5$ are independently selected from H and C$_{1-3}$alkyl, wherein the C$_{1-3}$alkyl is optionally substituted with one to two groups independently selected from —SO$_2$CH$_3$, —SO$_2$NH$_2$, OH, —OCH$_3$, —CN and a spiro C$_{3-5}$cycloalkyl group; or
R$^4$ and R$^5$ together with the N they are attached to may form a pyrrolidine ring, optionally substituted a group selected from —OH and —SO$_2$CH$_3$;
R$^6$ and R$^7$ are independently selected from H and CH$_3$; or together with the N they are attached to may form a pyrrolidine ring, optionally substituted with —OH;
and the pharmaceutically acceptable salts thereof.
In another embodiment, there are provided compounds of the formula I as described in any of the embodiments above, wherein
R$^1$ and R$^2$ are independently selected from H and C$_{1-3}$alkyl, provided that R$^1$ and R$^2$ are not both H; or
R$^1$ and R$^2$ may together form a spiro cyclobutyl ring;
R$^3$ is selected from
phenyl, substituted with one to two groups independently selected from —SO$_2$CH$_3$, —CN, —F, —C(O)NR$^4$R$^5$ and —O(CH$_2$)$_{2-3}$SO$_2$CH$_3$; and piperidin-4-yl, substituted on the nitrogen with —C(O)CH$_3$;
R$^4$ and R$^5$ are independently selected from H, and C$_{1-3}$alkyl, wherein the C$_{1-3}$alkyl is optionally substituted with one to two groups independently selected from —SO$_2$CH$_3$, —SO$_2$NH$_2$ and OH; or
R$^5$ and R$^5$ together with the N they are attached to may form a pyrrolidine ring, substituted with a —OH;
and the pharmaceutically acceptable salts thereof.
In another embodiment, there are provided compounds of the formula I as described in any of the embodiments above, wherein X is CH$_2$;
and the pharmaceutically acceptable salts thereof.
In another embodiment, there are provided compounds of the formula I as described in any of the embodiments above, wherein X is O;
and the pharmaceutically acceptable salts thereof.

In another aspect of the invention, there is provided a compound of the general formula I or a pharmaceutically acceptable salt thereof for use in a therapeutic method as described hereinbefore and hereinafter.

Table 1 shows representative compounds of the invention which can be made by the methods described in the general synthetic schemes, the examples, and known methods in the art.

TABLE 1

| Cpd No | STRUCTURE | Name |
|---|---|---|
| 1 | 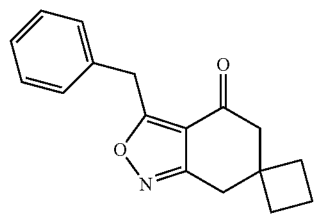 [SMILES: O=C1CC2(CCC2)Cc2noc(Cc3ccccc3)c21] | 6,6-spiro-cyclobutyl-3-benzyl-6,7-dihydro-5-H-benzo[c]isoxazole-4-one |
| 2 | 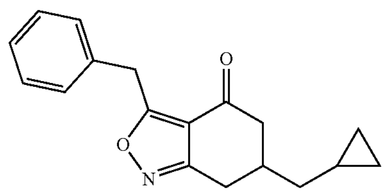 [SMILES: O=C1CC(CC2CC2)Cc2noc(Cc3ccccc3)c21] | 3-Benzyl-6-cyclopropylmethyl-6,7-dihydro-5H-benzo[c]isoxazol-4-one |
| 3 | 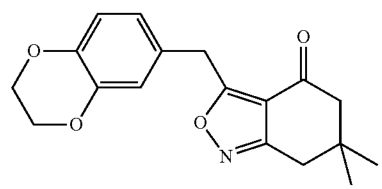 [SMILES: CC1(C)CC(=O)c2c(noc2Cc2ccc3c(c2)OCCO3)C1] | 3-(2,3-Dihydro-benzo[1,4]dioxin-6-ylmethyl)-6,6-dimethyl-6,7-dihydro-5H-benzo[c]isoxazol-4-one |
| 6 | 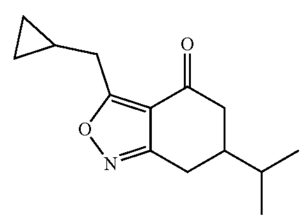 [SMILES: CC(C)C1CC(=O)c2c(noc2CC2CC2)C1] | 3-Cyclopropylmethyl-6-isopropyl-6,7-dihydro-5H-benzo[c]isoxazol-4-one |
| 7 | 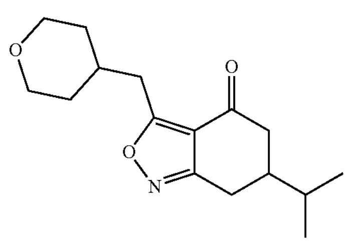 [SMILES: CC(C)C1CC(=O)c2c(noc2CC2CCOCC2)C1] | 6-Isopropyl-3-(tetrahydro-pyran-4-ylmethyl)-6,7-dihydro-5H-benzo[c]isoxazol-4-one |
| 8 | 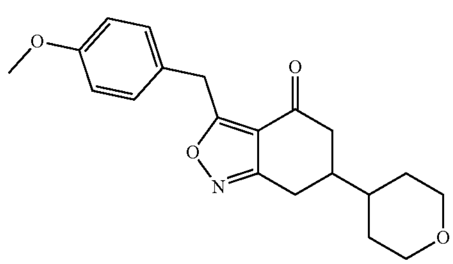 [SMILES: COc1ccc(Cc2onc3c2C(=O)CC(C2CCOCC2)C3)cc1] | 3-(4-Methoxy-benzyl)-6-(tetrahydro-pyran-4-yl)-6,7-dihydro-5H-benzo[c]isoxazol-4-one |

TABLE 1-continued

| Cpd No | STRUCTURE | Name |
|---|---|---|
| 9 | 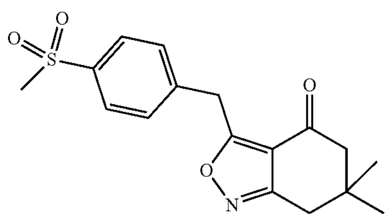 [SMILES: CC1(C)CC(=O)c2c(noc2Cc2ccc(S(C)(=O)=O)cc2)C1] | 3-(4-Methanesulfonyl-benzyl)-6,6-dimethyl-6,7-dihydro-5H-benzo[c]isoxazol-4-one |
| 10 | 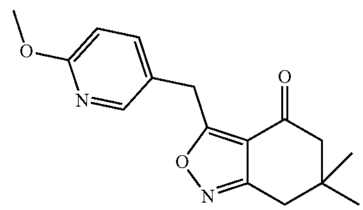 | 3-(6-Methoxy-pyridin-3-ylmethyl)-6,6-dimethyl-6,7-dihydro-5H-benzo[c]isoxazol-4-one |
| 11 | 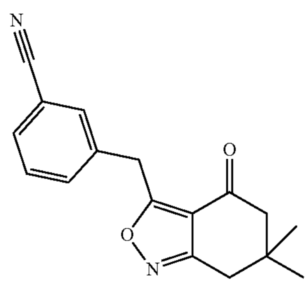 [SMILES: CC1(C)CC(=O)c2c(noc2Cc2cccc(C#N)c2)C1] | 3-(6,6-Dimethyl-4-oxo-4,5,6,7-tetrahydro-benzo[c]isoxazol-3-ylmethyl)-benzonitrile |
| 12 | 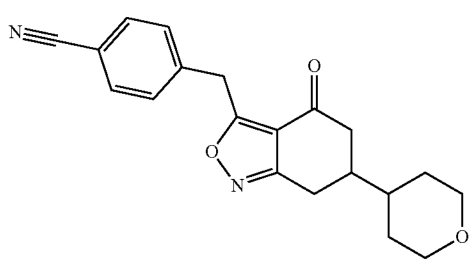 [SMILES: N#Cc1ccc(Cc2onc3c2C(=O)CC(C2CCOCC2)C3)cc1] | 4-[4-Oxo-6-(tetrahydro-pyran-4-yl)-4,5,6,7-tetrahydro-benzo[c]isoxazol-3-ylmethyl]-benzonitrile |
| 13 | 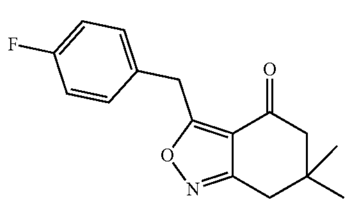 [SMILES: CC1(C)CC(=O)c2c(noc2Cc2ccc(F)cc2)C1] | 3-(4-Fluoro-benzyl)-6,6-dimethyl-6,7-dihydro-5H-benzo[c]isoxazol-4-one |
| 14 | 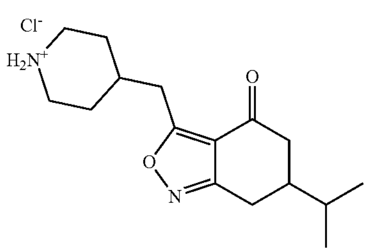 [SMILES: [Cl-] ; CC(C)C1CC(=O)c2c(noc2CC2CC[NH2+]CC2)C1] | 4-(6-Isopropyl-4-oxo-4,5,6,7-tetrahydro-benzo[c]isoxazol-3-ylmethyl)-piperidinium hydrochloride |

TABLE 1-continued

| Cpd No | STRUCTURE | Name |
|---|---|---|
| 15 | 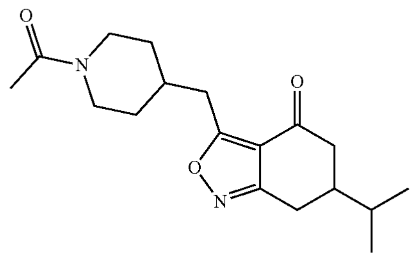 [SMILES: CC(=O)N1CCC(Cc2onc3c2C(=O)CC(C(C)C)C3)CC1] | 3-(1-Acetyl-piperidin-4-ylmethyl)-6-isopropyl-6,7-dihydro-5H-benzo[c]isoxazol-4-one |
| 16 | 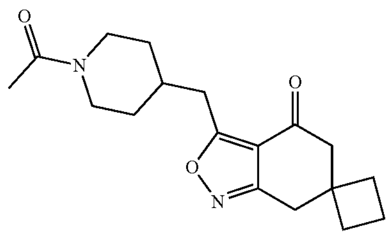 [SMILES: CC(=O)N1CCC(Cc2onc3c2C(=O)CC2(CCC2)C3)CC1] | 3-(1-Acetyl-piperidin-4-ylmethyl)-6,6-spiro-cyclobutyl-6,7-dihydro-5H-benzo[c]isoxazol-4-one |
| 17 | 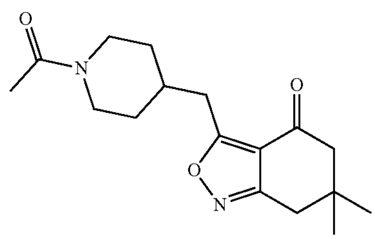 [SMILES: CC(=O)N1CCC(Cc2onc3c2C(=O)CC(C)(C)C3)CC1] | 3-(1-Acetyl-piperidin-4-ylmethyl)-6,6-dimethyl-6,7-dihydro-5H-benzo[c]isoxazol-4-one |
| 18 | 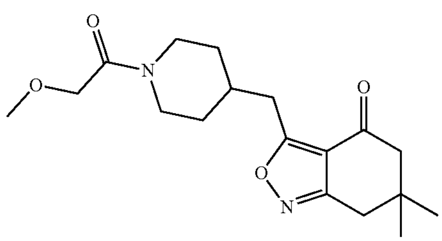 | 6-Isopropyl-3-[1-(2-methoxy-acetyl)-piperidin-4-ylmethyl]-6,7-dihydro-5H-benzo[c]isoxazol-4-one |
| 19 | 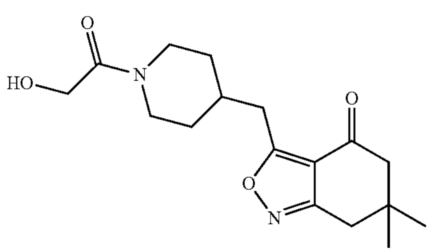 [SMILES: CC1(C)CC(=O)c2c(noc2CC2CCN(C(=O)CO)CC2)C1] | 3-[1-(2-Hydroxy-acetyl)-piperidin-4-ylmethyl]-6-isopropyl-6,7-dihydro-5H-benzo[c]isoxazol-4-one |
| 20 | 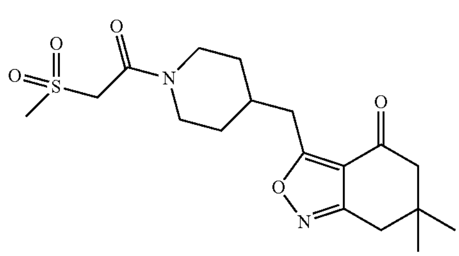 [SMILES: CC1(C)CC(=O)c2c(noc2CC2CCN(C(=O)CS(C)(=O)=O)CC2)C1] | 6-Isopropyl-3-[1-(2-methanesulfonyl-acetyl)-piperidin-4-ylmethyl]-6,7-dihydro-5H-benzo[c]isoxazol-4-one |

TABLE 1-continued

| Cpd No | STRUCTURE | Name |
|---|---|---|
| 21 | 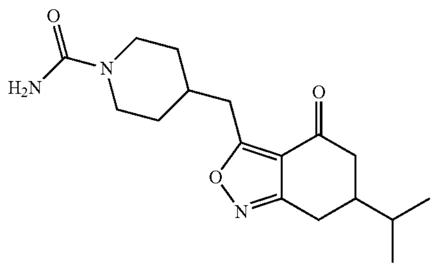 [SMILES: CC(C)C1CC(=O)c2c(noc2CC2CCN(C(N)=O)CC2)C1] | 4-(6-Isopropyl-4-oxo-4,5,6,7-tetrahydro-benzo[c]isoxazol-3-ylmethyl)-piperidine-1-carboxylic acid amide |
| 22 | 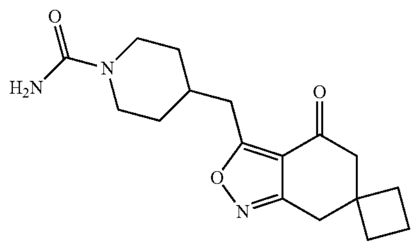 [SMILES: NC(=O)N1CCC(Cc2onc3c2C(=O)CC2(CCC2)C3)CC1] | 4-(6,6-spiro-cyclobutyl]-4-oxo-4,5,6,7-tetrahydro-benzo[c]isoxazol-3-ylmethyl)-piperidine-1-carboxylic acid amide |
| 23 | 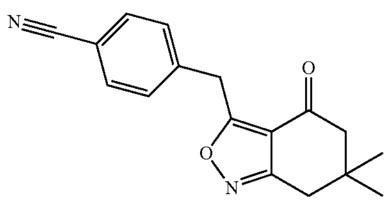 [SMILES: CC1(C)CC(=O)c2c(noc2Cc2ccc(C#N)cc2)C1] | 4-(6,6-Dimethyl-4-oxo-4,5,6,7-tetrahydro-benzo[c]isoxazol-3-ylmethyl)-benzonitrile |
| 24 | 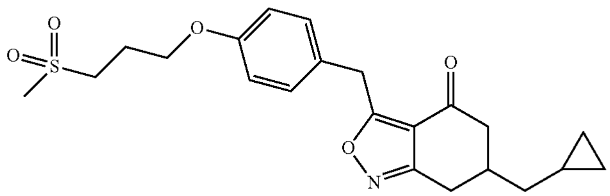 [SMILES: CS(=O)(=O)CCCOc1ccc(Cc2onc3c2C(=O)CC(CC2CC2)C3)cc1] | 6-Cyclopropylmethyl-3-[4-(3-methanesulfonyl-propoxy)-benzyl]-6,7-dihydro-5H-benzo[c]isoxazol-4-one |
| 25 | 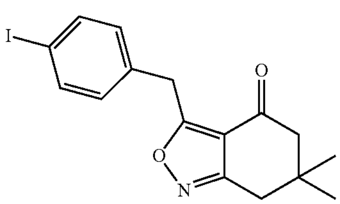 [SMILES: CC1(C)CC(=O)c2c(noc2Cc2ccc(I)cc2)C1] | 3-(4-Iodo-benzyl)-6,6-dimethyl-6,7-dihydro-5H-benzo[c]isoxazol-4-one |
| 26 | 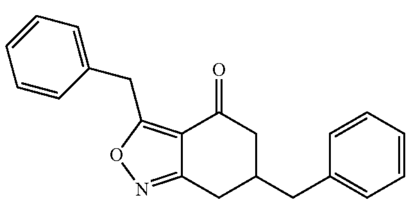 [SMILES: O=C1CC(Cc2ccccc2)Cc2noc(Cc3ccccc3)c21] | 3,6-Dibenzyl-6,7-dihydro-5H-benzo[c]isoxazol-4-one |
| 27 | 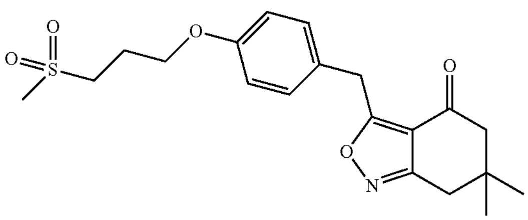 [SMILES: CC1(C)CC(=O)c2c(noc2Cc2ccc(OCCCS(C)(=O)=O)cc2)C1] | 3-[4-(3-Methanesulfonyl-propoxy)-benzyl]-6,6-dimethyl-6,7-dihydro-5H-benzo[c]isoxazol-4-one |

TABLE 1-continued

| Cpd No | STRUCTURE | Name |
|---|---|---|
| 28 | 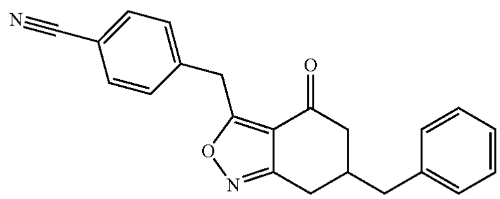 [SMILES: N#Cc1ccc(Cc2onc3c2C(=O)CC(Cc2ccccc2)C3)cc1] | 4-(6-Benzyl-4-oxo-4,5,6,7-tetrahydro-benzo[c]isoxazol-3-ylmethyl)-benzonitrile |
| 29 | 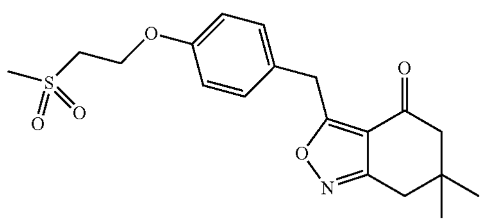 | 3-[4-(2-Methanesulfonyl-ethoxy)-benzyl]-6,6-dimethyl-6,7-dihydro-5H-benzo[c]isoxazol-4-one |
| 30 | 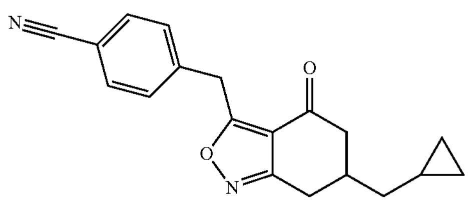 [SMILES: N#Cc1ccc(Cc2onc3c2C(=O)CC(CC2CC2)C3)cc1] | 4-(6-Cyclopropylmethyl-4-oxo-4,5,6,7-tetrahydro-benzo[c]isoxazol-3-ylmethyl)-benzonitrile |
| 31 | 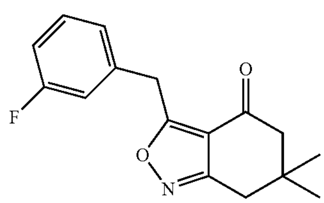 [SMILES: CC1(C)CC(=O)c2c(noc2Cc2cccc(F)c2)C1] | 3-(3-Fluoro-benzyl)-6,6-dimethyl-6,7-dihydro-5H-benzo[c]isoxazol-4-one |
| 33 | 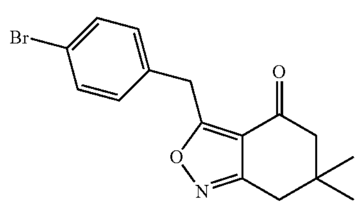 [SMILES: CC1(C)CC(=O)c2c(noc2Cc2ccc(Br)cc2)C1] | 3-(4-Bromo-benzyl)-6,6-dimethyl-6,7-dihydro-5H-benzo[c]isoxazol-4-one |
| 34 | 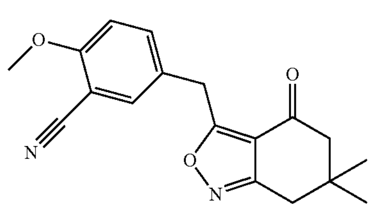 | 5-(6,6-Dimethyl-4-oxo-4,5,6,7-tetrahydro-benzo[c]isoxazol-3-ylmethyl)-2-methoxy-benzonitrile |
| 35 | 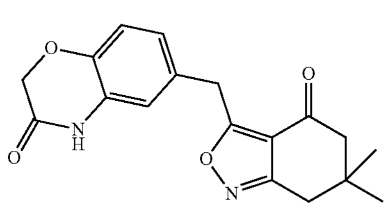 [SMILES: CC1(C)CC(=O)c2c(noc2Cc2ccc3c(c2)NC(=O)CO3)C1] | 6-(6,6-Dimethyl-4-oxo-4,5,6,7-tetrahydro-benzo[c]isoxazol-3-ylmethyl)-4H-benzo[1,4]oxazin-3-one |

TABLE 1-continued

| Cpd No | STRUCTURE | Name |
|---|---|---|
| 36 | 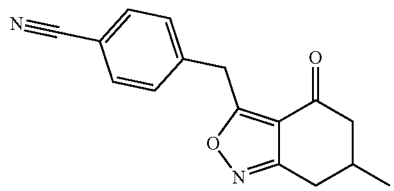 [SMILES: CC1CC(=O)c2c(noc2Cc2ccc(C#N)cc2)C1] | 4-(6-Methyl-4-oxo-4,5,6,7-tetrahydro-benzo[c]isoxazol-3-ylmethyl)-benzonitrile |
| 37 | 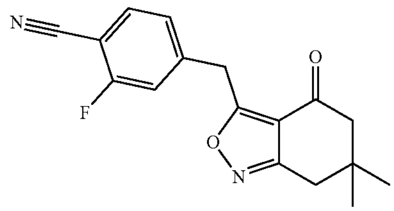 [SMILES: CC1(C)CC(=O)c2c(noc2Cc2ccc(C#N)c(F)c2)C1] | 4-(6,6-Dimethyl-4-oxo-4,5,6,7-tetra hydro-benzo[c]isoxazol-3-ylmethyl)-2-fluoro-benzonitrile |
| 38 | 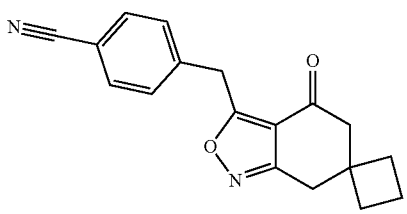 [SMILES: N#Cc1ccc(Cc2onc3c2C(=O)CC2(CCC2)C3)cc1] | 4-(-6,6-spiro-cyclobutyl-4-oxo-4,5,6,7-tetrahydro-benzo[c]isoxazol-3-ylmethyl)-benzonitrile |
| 39 | 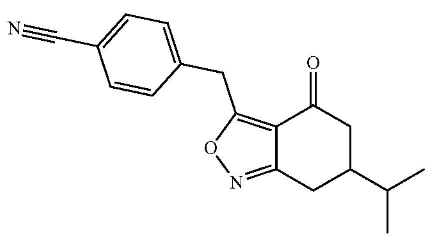 [SMILES: CC(C)C1CC(=O)c2c(noc2Cc2ccc(C#N)cc2)C1] | 4-(-6-Isopropyl-4-oxo-4,5,6,7-tetrahydro-benzo[c]isoxazol-3-ylmethyl)-benzonitrile |
| 40 | 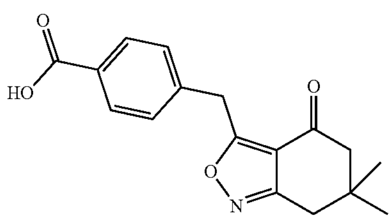 [SMILES: CC1(C)CC(=O)c2c(noc2Cc2ccc(C(=O)O)cc2)C1] | 4-(6,6-Dimethyl-4-oxo-4,5,6,7-tetrahydro-benzo[c]isoxazol-3-ylmethyl)-benzoic acid |
| 41 | 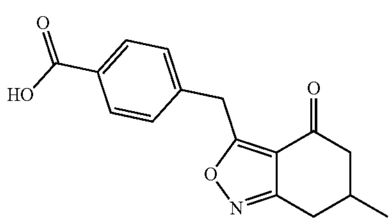 [SMILES: CC1CC(=O)c2c(noc2Cc2ccc(C(=O)O)cc2)C1] | 4-(6-Methyl-4-oxo-4,5,6,7-tetrahydro-benzo[c]isoxazol-3-ylmethyl)-benzoic acid |
| 42 | 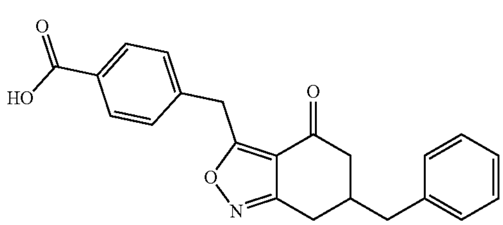 [SMILES: O=C(O)c1ccc(Cc2onc3c2C(=O)CC(Cc2ccccc2)C3)cc1] | 4-(6-Benzyl-4-oxo-4,5,6,7-tetrahydro-benzo[c]isoxazol-3-ylmethyl)-benzoic acid |

TABLE 1-continued

| Cpd No | STRUCTURE | Name |
|---|---|---|
| 43 | 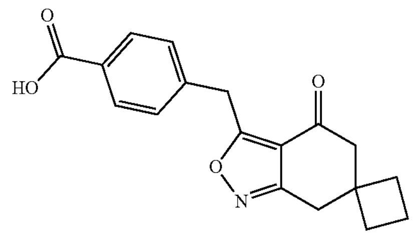 [SMILES: O=C(O)c1ccc(Cc2onc3c2C(=O)CC2(CCC2)C3)cc1] | 4-(-6,6-spiro-cyclobutyl-4-oxo-4,5,6,7-tetrahydro-benzo[c]isoxazol-3-ylmethyl)-benzoic acid |
| 44 | 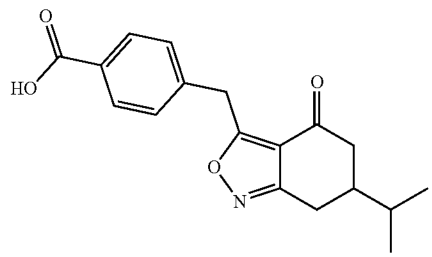 [SMILES: CC(C)C1CC(=O)c2c(noc2Cc2ccc(C(=O)O)cc2)C1] | 4-(6-Isopropyl-4-oxo-4,5,6,7-tetrahydro-benzo[c]isoxazol-3-ylmethyl)-benzoic acid |
| 45 | 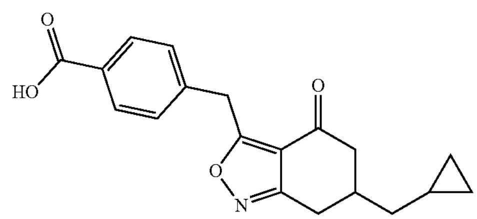 [SMILES: O=C(O)c1ccc(Cc2onc3c2C(=O)CC(CC2CC2)C3)cc1] | 4-(6-Cyclopropylmethyl-4-oxo-4,5,6,7-tetrahydro-benzo[c]isoxazol-3-ylmethyl)-benzoic acid |
| 46 | 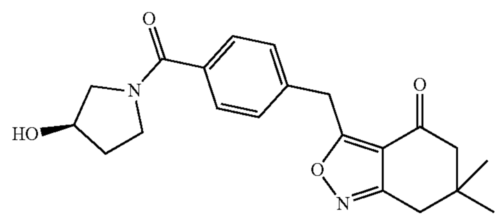 [SMILES: CC1(C)CC(=O)c2c(noc2Cc2ccc(C(=O)N3CC[C@@H](O)C3)cc2)C1] | 3-[4-((R)-3-Hydroxy-pyrrolidine-1-carbonyl)-benzyl]-6,6-dimethyl-6,7-dihydro-5H-benzo[c]isoxazol-4-one |
| 47 | 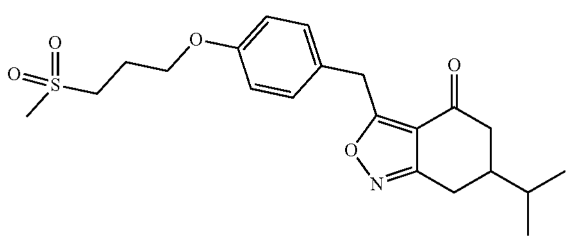 [SMILES: CC(C)C1CC(=O)c2c(noc2Cc2ccc(OCCCS(C)(=O)=O)cc2)C1] | 6-Isopropyl-3-[4-(3-methanesulfonyl-propoxy)-benzyl]-6,7-dihydro-5H-benzo[c]isoxazol-4-one |
| 48 | 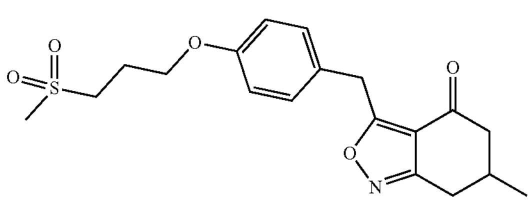 [SMILES: CC1CC(=O)c2c(noc2Cc2ccc(OCCCS(C)(=O)=O)cc2)C1] | 3-[4-(3-Methanesulfonyl-propoxy)-benzyl]-6-methyl-6,7-dihydro-5H-benzo[c]isoxazol-4-one |
| 49 | 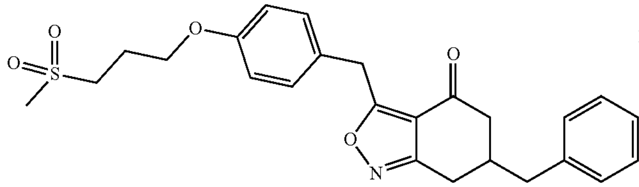 [SMILES: CS(=O)(=O)CCCOc1ccc(Cc2onc3c2C(=O)CC(Cc2ccccc2)C3)cc1] | 6-Benzyl-3-[4-(3-methanesulfonyl-propoxy)-benzyl]-6,7-dihydro-5H-benzo[c]isoxazol-4-one |

TABLE 1-continued

| Cpd No | STRUCTURE | Name |
|---|---|---|
| 50 | 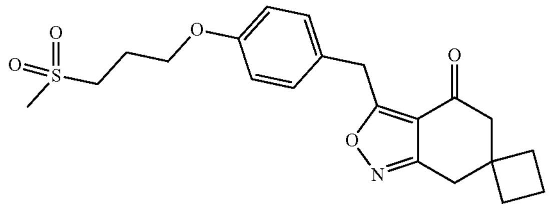 [SMILES: CS(=O)(=O)CCCOc1ccc(Cc2onc3c2C(=O)CC2(CCC2)C3)cc1] | 3-[4-(3-Methanesulfonyl-propoxy)-benzyl]-6-6-spirocyclebutyl-6,7-dihydro-5H-benzo[c]isoxazol-4-one |
| 51 | 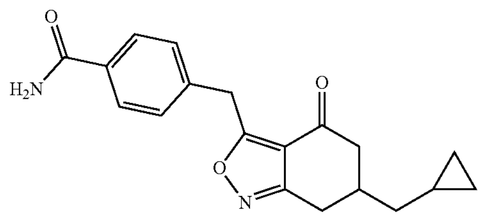 [SMILES: NC(=O)c1ccc(Cc2onc3c2C(=O)CC(CC2CC2)C3)cc1] | 4-(6-Cyclopropylmethyl-4-oxo-4,5,6,7-tetrahydro-benzo[c]isoxazol-3-ylmethyl)-benzamide |
| 52 | 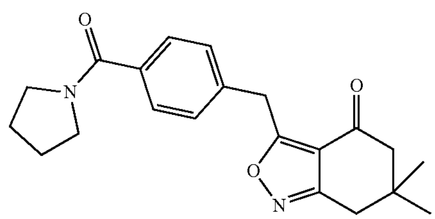 [SMILES: CC1(C)CC(=O)c2c(noc2Cc2ccc(C(=O)N3CCCC3)cc2)C1] | 6,6-Dimethyl-3-[4-(pyrrolidine-1-carbonyl)-benzyl]-6,7-dihydro-5H-benzo[c]isoxazol-4-one |
| 53 | 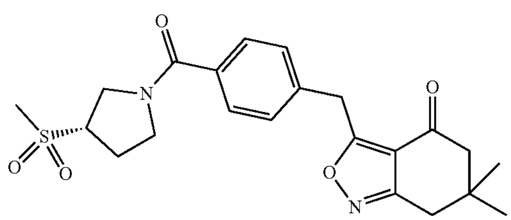 [SMILES: CC1(C)CC(=O)c2c(noc2Cc2ccc(C(=O)N3CC[C@H](S(C)(=O)=O)C3)cc2)C1] | 3-[4-((S)-3-Methanesulfonyl-pyrrolidine-1-carbonyl)-benzyl]-6,6-dimethyl-6,7-dihydro-5H-benzo[c]isoxazol-4-one |
| 54 | 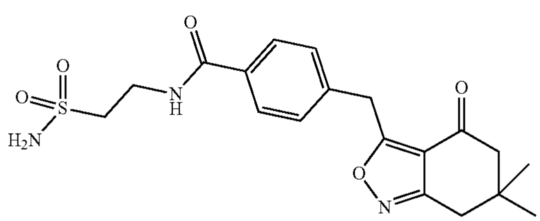 [SMILES: CC1(C)CC(=O)c2c(noc2Cc2ccc(C(=O)NCCS(N)(=O)=O)cc2)C1] | 4-(6,6-Dimethyl-4-oxo-4,5,6,7-tetrahydro-benzo[c]isoxazol-3-ylmethyl)-N-(2-sulfamoyl-ethyl)-benzamide |
| 55 | 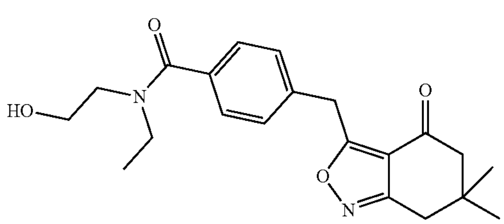 [SMILES: CCN(CCO)C(=O)c1ccc(Cc2onc3c2C(=O)CC(C)(C)C3)cc1] | 4-(6,6-Dimethyl-4-oxo-4,5,6,7-tetrahydro-benzo[c]isoxazol-3-ylmethyl)-N-ethyl-N-(2-hydroxy-ethyl)-benzamide |
| 56 | 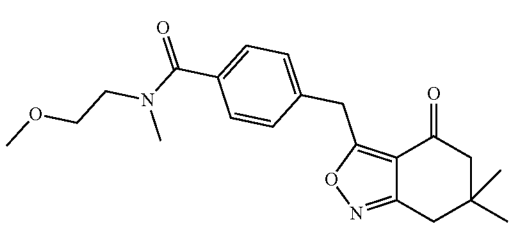 | 4-(6,6-Dimethyl-4-oxo-4,5,6,7-tetrahydro-benzo[c]isoxazol-3-ylmethyl)-N-(2-methoxy-ethyl)-N-methyl-benzamide |

TABLE 1-continued

| Cpd No | STRUCTURE | Name |
|---|---|---|
| 57 | 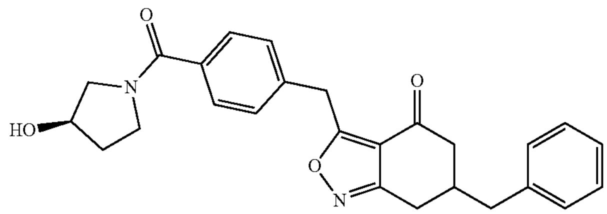 [SMILES: O=C1CC(Cc2ccccc2)Cc2noc(Cc3ccc(C(=O)N4CC[C@@H](O)C4)cc3)c21] | 6-Benzyl-3-[4-((R)-3-hydroxy-pyrrolidine-1-carbonyl)-benzyl]-6,7-dihydro-5H-benzo[c]isoxazol-4-one |
| 58 | 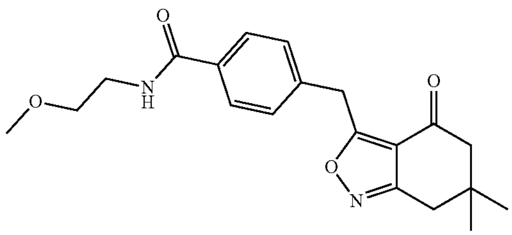 | 4-(6,6-Dimethyl-4-oxo-4,5,6,7-tetrahydro-benzo[c]isoxazol-3-ylmethyl)-N-(2-methoxy-ethyl)-benzamide |
| 59 | 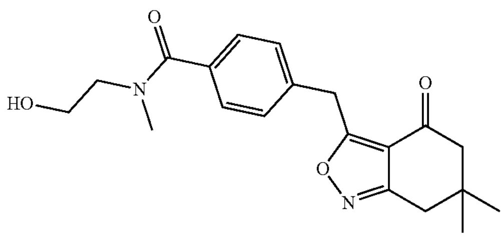 | 4-(6,6-Dimethyl-4-oxo-4,5,6,7-tetrahydro-benzo[c]isoxazol-3-ylmethyl)-N-(2-hydroxy-ethyl)-N-methyl-benzamide |
| 60 | 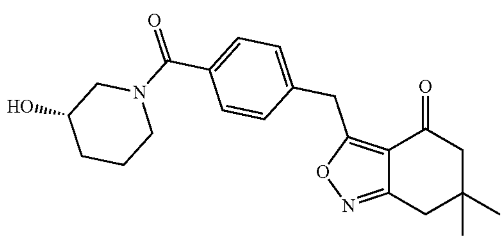 [SMILES: CC1(C)CC(=O)c2c(noc2Cc2ccc(C(=O)N3CCC[C@H](O)C3)cc2)C1] | 3-[4-((S)-3-Hydroxy-piperidine-1-carbonyl)-benzyl]-6,6-dimethyl-6,7-dihydro-5H-benzo[c]isoxazol-4-one |
| 61 | 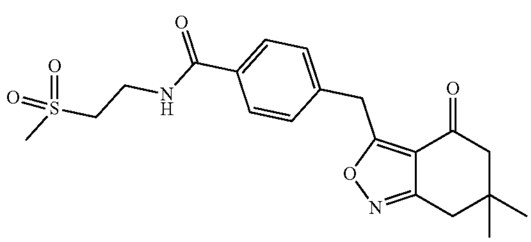 [SMILES: CC1(C)CC(=O)c2c(noc2Cc2ccc(C(=O)NCCS(C)(=O)=O)cc2)C1] | 4-(6,6-Dimethyl-4-oxo-4,5,6,7-tetrahydro-benzo[c]isoxazol-3-ylmethyl)-N-(2-methanesulfonyl-ethyl)-benzamide |
| 62 | 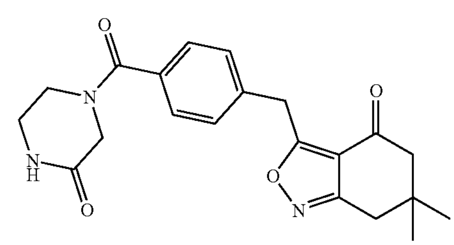 [SMILES: CC1(C)CC(=O)c2c(noc2Cc2ccc(C(=O)N3CCNC(=O)C3)cc2)C1] | 6,6-Dimethyl-3-[4-(3-oxo-piperazine-1-carbonyl)-benzyl]-6,7-dihydro-5H-benzo[c]isoxazol-4-one |

TABLE 1-continued

| Cpd No | STRUCTURE | Name |
|---|---|---|
| 63 | 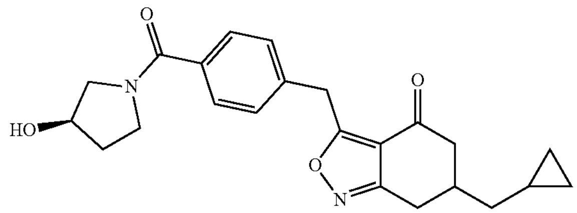 [SMILES: O=C1CC(CC2CC2)Cc2noc(Cc3ccc(C(=O)N4CC[C@@H](O)C4)cc3)c21] | 6-Cyclopropylmethyl-3-[4-((R)-3-hydroxy-pyrrolidine-1-carbonyl)-benzyl]-6,7-dihydro-5H-benzo[c]isoxazol-4-one |
| 64 | 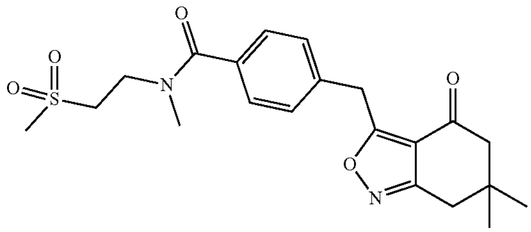 [SMILES: CN(CCS(C)(=O)=O)C(=O)c1ccc(Cc2onc3c2C(=O)CC(C)(C)C3)cc1] | 4-(6,6-Dimethyl-4-oxo-4,5,6,7-tetrahydro-benzo[c]isoxazol-3-ylmethyl)-N-(2-methanesulfonyl-ethyl)-N-methyl-benzamide |
| 65 | 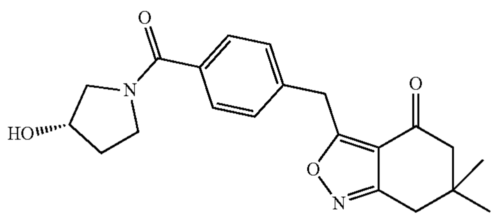 [SMILES: CC1(C)CC(=O)c2c(noc2Cc2ccc(C(=O)N3CC[C@H](O)C3)cc2)C1] | 3-[4-((S)-3-Hydroxy-pyrrolidine-1-carbonyl)-benzyl]-6,6-dimethyl-6,7-dihydro-5H-benzo[c]isoxazol-4-one |
| 66 | 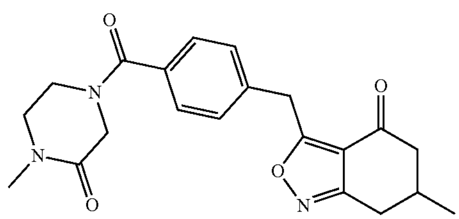 | 6-Methyl-3-[4-(4-methyl-3-oxo-piperazine-1-carbonyl)-benzyl]-6,7-dihydro-5H-benzo[c]isoxazol-4-one |
| 67 | 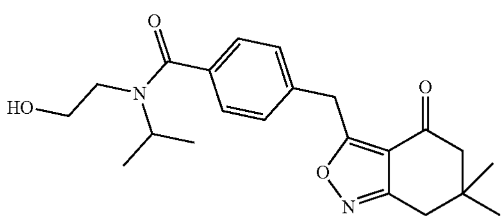 [SMILES: CC(C)N(CCO)C(=O)c1ccc(Cc2onc3c2C(=O)CC(C)(C)C3)cc1] | 4-(6,6-Dimethyl-4-oxo-4,5,6,7-tetrahydro-benzo[c]isoxazol-3-ylmethyl)-N-(2-hydroxy-ethyl)-N-isopropyl-benzamide |
| 68 | 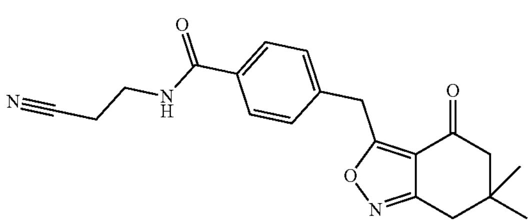 [SMILES: CC1(C)CC(=O)c2c(noc2Cc2ccc(C(=O)NCCC#N)cc2)C1] | N-(2-Cyano-ethyl)-4-(6,6-dimethyl-4-oxo-4,5,6,7-tetrahydro-benzo[c]isoxazol-3-ylmethyl)-benzamide |
| 69 | 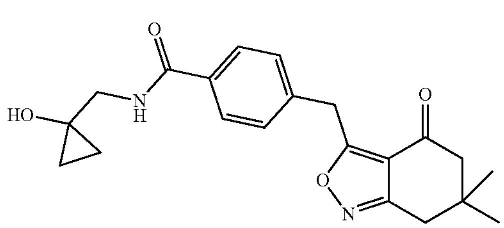 [SMILES: CC1(C)CC(=O)c2c(noc2Cc2ccc(C(=O)NCC3(O)CC3)cc2)C1] | 4-(6,6-Dimethyl-4-oxo-4,5,6,7-tetrahydro-benzo[c]isoxazol-3-ylmethyl)-N-(1-hydroxy-cyclopropylmethyl)-benzamide |

TABLE 1-continued

| Cpd No | STRUCTURE | Name |
|---|---|---|
| 70 | 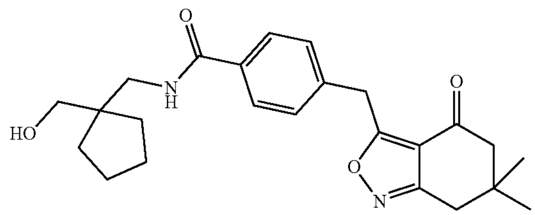 [SMILES: CC1(C)CC(=O)c2c(noc2Cc2ccc(C(=O)NCC3(CO)CCCC3)cc2)C1] | 4-(6,6-Dimethyl-4-oxo-4,5,6,7-tetrahydro-benzo[c]isoxazol-3-ylmethyl)-N-(1-hydroxymethyl-cyclopentylmethyl)-benzamide |
| 71 | 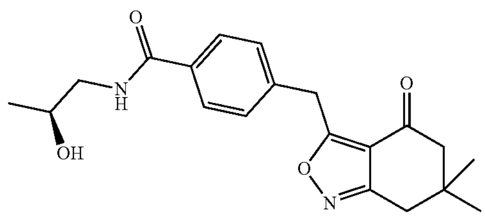 [SMILES: C[C@H](O)CNC(=O)c1ccc(Cc2onc3c2C(=O)CC(C)(C)C3)cc1] | 4-(6,6-Dimethyl-4-oxo-4,5,6,7-tetrahydro-benzo[c]isoxazol-3-ylmethyl)-N-((S)-2-hydroxy-propyl)-benzamide |
| 72 | 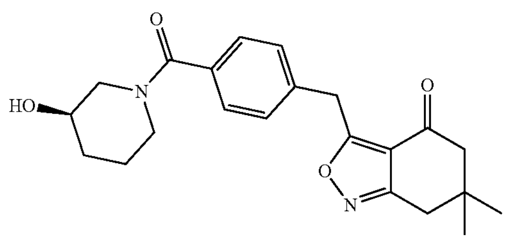 [SMILES: CC1(C)CC(=O)c2c(noc2Cc2ccc(C(=O)N3CCC[C@@H](O)C3)cc2)C1] | 3-[4-((R)-3-Hydroxy-piperidine-1-carbonyl)-benzyl]-6,6-dimethyl-6,7-dihydro-5H-benzo[c]isoxazol-4-one |
| 73 | 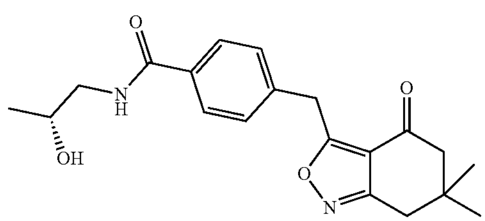 [SMILES: C[C@@H](O)CNC(=O)c1ccc(Cc2onc3c2C(=O)CC(C)(C)C3)cc1] | 4-(6,6-Dimethyl-4-oxo-4,5,6,7-tetrahydro-benzo[c]isoxazol-3-ylmethyl)-N-((R)-2-hydroxy-propyl)-benzamide |
| 74 | 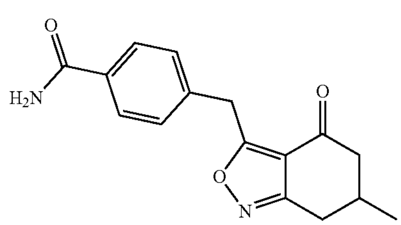 [SMILES: CC1CC(=O)c2c(noc2Cc2ccc(C(N)=O)cc2)C1] | 4-(6-Methyl-4-oxo-4,5,6,7-tetrahydro-benzo[c]isoxazol-3-ylmethyl)-benzamide |
| 75 | 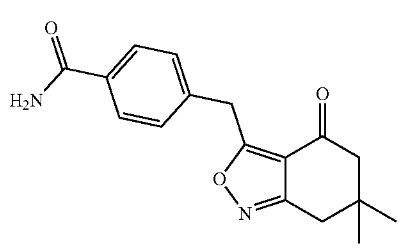 [SMILES: CC1(C)CC(=O)c2c(noc2Cc2ccc(C(N)=O)cc2)C1] | 4-(6,6-Dimethyl-4-oxo-4,5,6,7-tetrahydro-benzo[c]isoxazol-3-ylmethyl)-benzamide |

TABLE 1-continued

| Cpd No | STRUCTURE | Name |
|---|---|---|
| 76 | 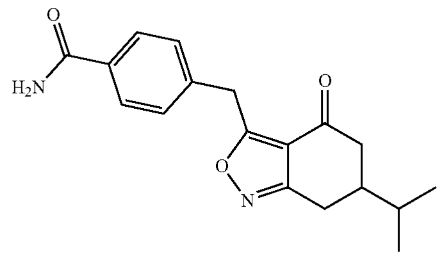 [SMILES: CC(C)C1CC(=O)c2c(noc2Cc2ccc(C(N)=O)cc2)C1] | 4-(6-Isopropyl-4-oxo-4,5,6,7-tetrahydro-benzo[c]isoxazol-3-ylmethyl)-benzamide |
| 77 | 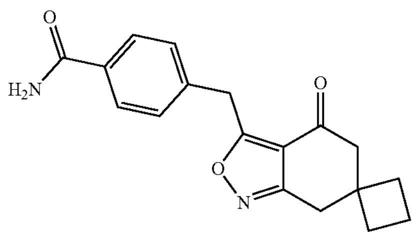 [SMILES: NC(=O)c1ccc(Cc2onc3c2C(=O)CC2(CCC2)C3)cc1] | 4-(-6,6-spiro-cyclobutyl-4-oxo-4,5,6,7-tetrahydro-benzo[c]isoxazol-3-ylmethyl)-benzamide |
| 78 | 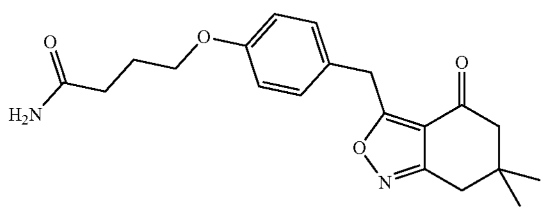 [SMILES: CC1(C)CC(=O)c2c(noc2Cc2ccc(OCCCC(N)=O)cc2)C1] | 4-[4-(6,6-Dimethyl-4-oxo-4,5,6,7-tetrahydro-benzo[c]isoxazol-3-ylmethyl)-phenoxyl-butyramide |
| 79 | 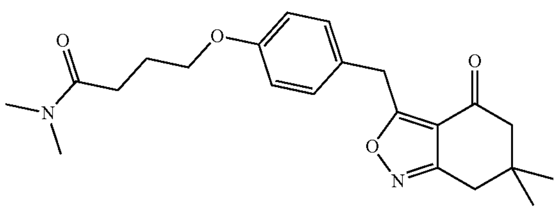 | 4-[4-(6,6-Dimethyl-4-oxo-4,5,6,7-tetrahydro-benzo[c]isoxazol-3-ylmethyl)-phenoxyl-N,N-dimethyl-butyramide |
| 80 | 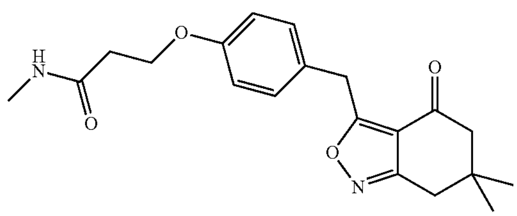 | 3-[4-(6,6-Dimethyl-4-oxo-4,5,6,7-tetrahydro-benzo[c]isoxazol-3-ylmethyl)-phenoxy]-N-methyl-propionamide |
| 81 | 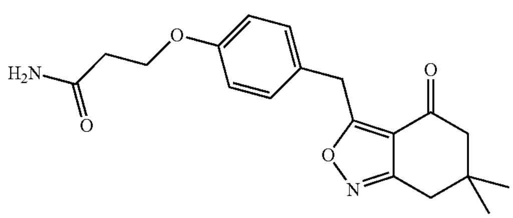 [SMILES: CC1(C)CC(=O)c2c(noc2Cc2ccc(OCCC(N)=O)cc2)C1] | 3-[4-(6,6-Dimethyl-4-oxo-4,5,6,7-tetrahydro-benzo[c]isoxazol-3-ylmethyl)-phenoxy]-propionamide |
| 82 | 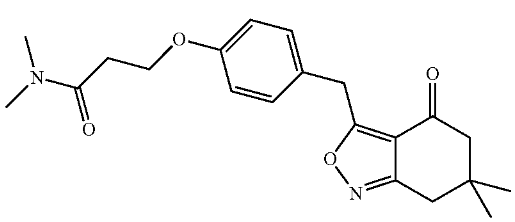 | 3-[4-(6,6-Dimethyl-4-oxo-4,5,6,7-tetrahydro-benzo[c]isoxazol-3-ylmethyl)-phenoxy]-N,N-dimethyl-propionamide |

TABLE 1-continued

| Cpd No | STRUCTURE | Name |
|---|---|---|
| 83 | 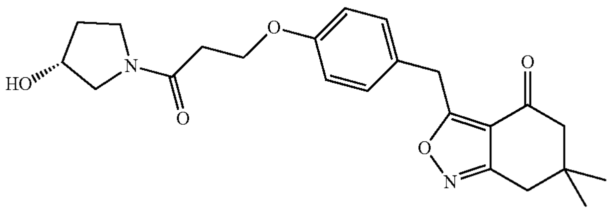 [SMILES: CC1(C)CC(=O)c2c(noc2Cc2ccc(OCCC(=O)N3CC[C@@H](O)C3)cc2)C1] | 3-{4-[3-((R)-3-Hydroxy-pyrrolidin-1-yl)-3-oxo-propoxy]-benzyl}-6,6-dimethyl-6,7-dihydro-5H-benzo[c]isoxazol-4-one |
| 84 | 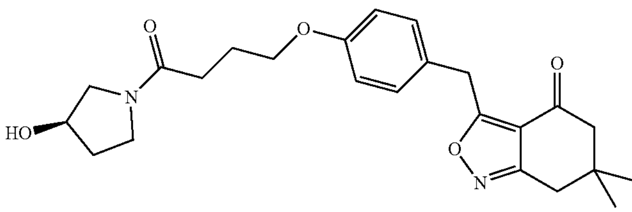 [SMILES: CC1(C)CC(=O)c2c(noc2Cc2ccc(OCCCC(=O)N3CC[C@@H](O)C3)cc2)C1] | 3-{4-[4-((R)-3-Hydroxy-pyrrolidin-1-yl)-4-oxo-butoxy]-benzyl}-6,6-dimethyl-6,7-dihydro-5H-benzo[c]isoxazol-4-one |
| 85 | 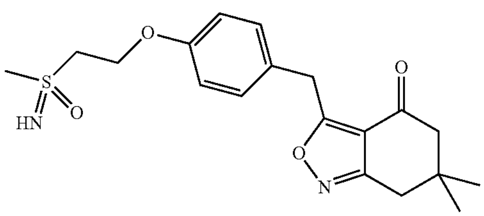 | 3-[4-(2-Methanesulfoximine-ethoxy)-benzyl]-6,6-dimethyl-6,7-dihydro-5H-benzo[c]isoxazol-4-one |
| 87 | 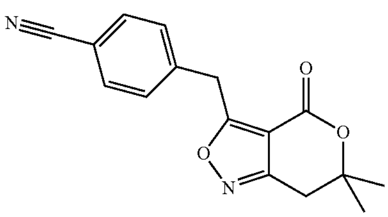 [SMILES: CC1(C)Cc2noc(Cc3ccc(C#N)cc3)c2C(=O)O1] | 4-(6,6-Dimethyl-4-oxo-6,7-dihydro-4H-pyrano[4,3-c]isoxazol-3-ylmethyl)-benzonitrile |
| 88 | 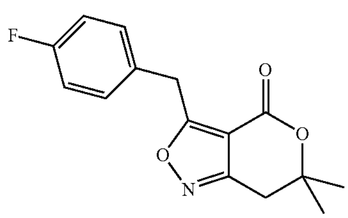 [SMILES: CC1(C)Cc2noc(Cc3ccc(F)cc3)c2C(=O)O1] | 3-(4-Fluoro-benzyl)-6,6-dimethyl-6,7-dihydro-pyrano[4,3-c]isoxazol-4-one |
| 89 | 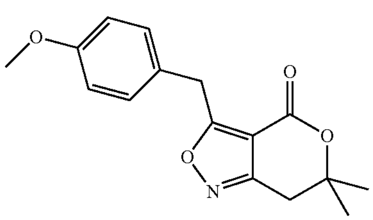 | 3-(4-Methoxy-benzyl)-6,6-dimethyl-6,7-dihydro-pyrano[4,3-c]isoxazol-4-one |
| 90 | 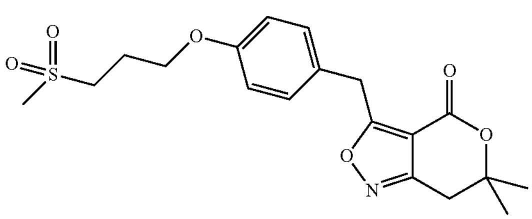 [SMILES: CC1(C)Cc2noc(Cc3ccc(OCCCS(C)(=O)=O)cc3)c2C(=O)O1] | 3-[4-(3-Methanesulfonyl-propoxy)-benzyl]-6,6-dimethyl-6,7-dihydro-pyrano[4,3-c]isoxazol-4-one |

TABLE 1-continued

| Cpd No | STRUCTURE | Name |
|---|---|---|
| 91 | 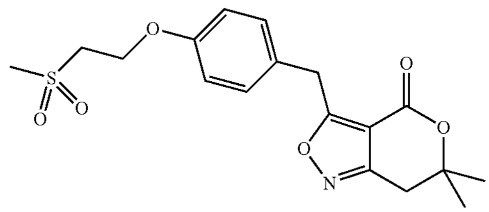 | 3-[4-(2-Methanesulfonyl-ethoxy)-benzyl]-6,6-dimethyl-6,7-dihydro-pyrano[4,3-c]isoxazol-4-one |
| 92 | 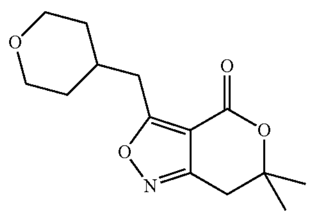 [SMILES: CC1(C)Cc2noc(CC3CCOCC3)c2C(=O)O1] | 6,6-Dimethyl-3-(tetrahydro-pyran-4-ylmethyl)-6,7-dihydro-pyrano[4,3-c]isoxazol-4-one |
| 93 | 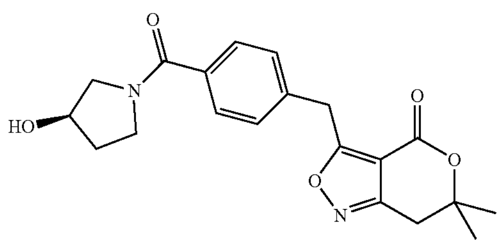 [SMILES: CC1(C)Cc2noc(Cc3ccc(C(=O)N4CC[C@@H](O)C4)cc3)c2C(=O)O1] | 3-[4-((R)-3-Hydroxy-pyrrolidine-1-carbonyl)-benzyl]-6,6-dimethyl-6,7-dihydro-pyrano[4,3-c]isoxazol-4-one |
| 94 | 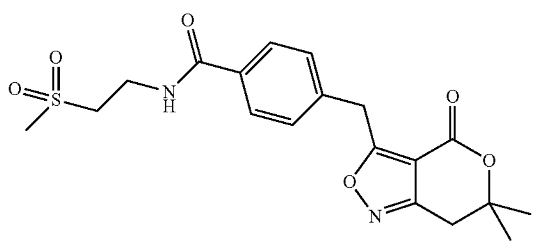 [SMILES: CC1(C)Cc2noc(Cc3ccc(C(=O)NCCS(C)(=O)=O)cc3)c2C(=O)O1] | 4-(6,6-Dimethyl-4-oxo-6,7-dihydro-4H-pyrano[4,3-c]isoxazol-3-ylmethyl)-N-(2-methanesulfonyl-ethyl)-benzamide |
| 95 | 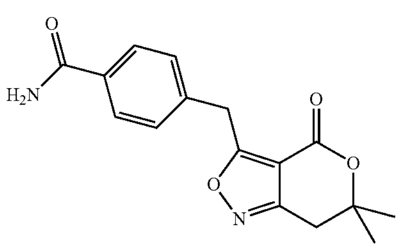 [SMILES: CC1(C)Cc2noc(Cc3ccc(C(N)=O)cc3)c2C(=O)O1] | 4-(6,6-Dimethyl-4-oxo-6,7-dihydro-4H-pyrano[4,3-c]isoxazol-3-ylmethyl)-benzamide |
| 96 | 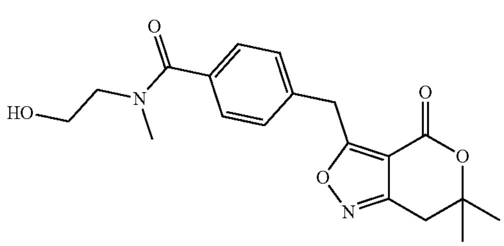 [SMILES: CN(CCO)C(=O)c1ccc(Cc2onc3c2C(=O)OC(C)(C)C3)cc1] | 4-(6,6-Dimethyl-4-oxo-6,7-dihydro-4H-pyrano[4,3-c]isoxazol-3-ylmethyl)-N-(2-hydroxy-ethyl)-N-methyl-benzamide |

TABLE 1-continued

| Cpd No | STRUCTURE | Name |
|---|---|---|
| 97 | 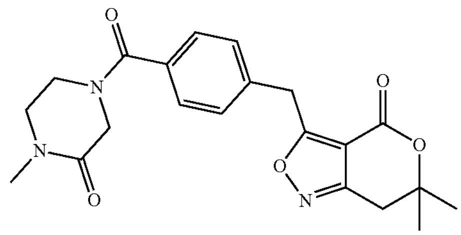 | 6,6-Dimethyl-3-[4-(4-methyl-3-oxo-piperazine-1-carbonyl)-benzyl]-6,7-dihydro-pyrano[4,3-c]isoxazol-4-one |

In one embodiment, the invention relates to a compound selected from the group consisting of compounds 1-3, 6-31 and 33-85 and 87-97 depicted in Table 1 above and the pharmaceutically acceptable salts thereof.

In another embodiment, the invention relates to compounds 9, 13, 15-17, 23, 25, 27, 29, 39, 46, 54, 59, 61, 65, 75, 90, 93, 94 depicted in Table 1 above and the pharmaceutically acceptable salts thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound. Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates, esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, peroxides or a compound which would have a 'dangling valency', or a 'carbanion' are not compounds contemplated by the inventive methods disclosed herein.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —$(CH_2)$—, —$(CH_2—CH_2)$—, —$(CH(CH_3))$—, —$(CH_2—CH_2—CH_2)$—, —$(C(CH_3)_2)$—, —$(CH(CH_2CH_3))$—, —$(CH(CH_3)—CH_2)$—, —$(CH_2—CH(CH_3))$—, —$(CH_2—CH_2—CH_2—CH_2)$—, —$(CH_2—CH_2—CH(CH_3))$—, —$(CH(CH_3)—CH_2—CH_2)$—, —$(CH_2—CH(CH_3)—CH_2)$—, —$(CH_2—C(CH_3)_2)$—, —$(C(CH_3)_2—CH_2)$—, —$(CH(CH_3)—CH(CH_3))$—, —$(CH_2—CH(CH_2CH_3))$—, —$(CH(CH_2CH_3)—CH_2)$—, —$(CH(CH_2CH_2CH_3))$—, —$(CHCH(CH_3)_2)$— and —$C(CH_3)(CH_2CH_3)$—.

The term "$C_{3-x}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, tetrahydroquinolinyl, isoquinolinyl, quinazolinyl, indazolyl, thieno[2,3-d]pyrimidinyl, indolyl, isoindolyl, benzofuranyl, dihydrobenzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —$CH_2CHF_2$, —$CF_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl, likewise, —S—$R_a$ may be represented as phenyl-S(O)$_m$— when $R_a$ is phenyl and where m is 0, 1 or 2.

General Synthetic Methods

The compounds of the invention may be prepared by the methods and examples presented below and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided below. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

Compounds of formula (I) wherein X=CH$_2$ may be prepared as illustrated in Scheme 1.

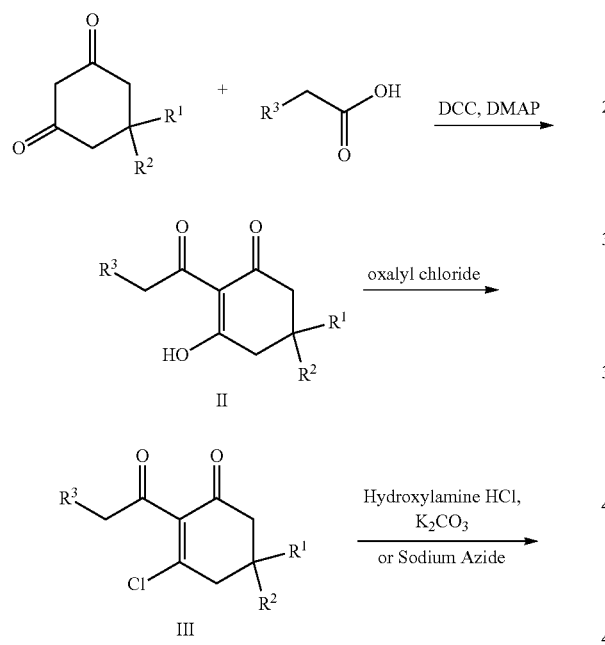

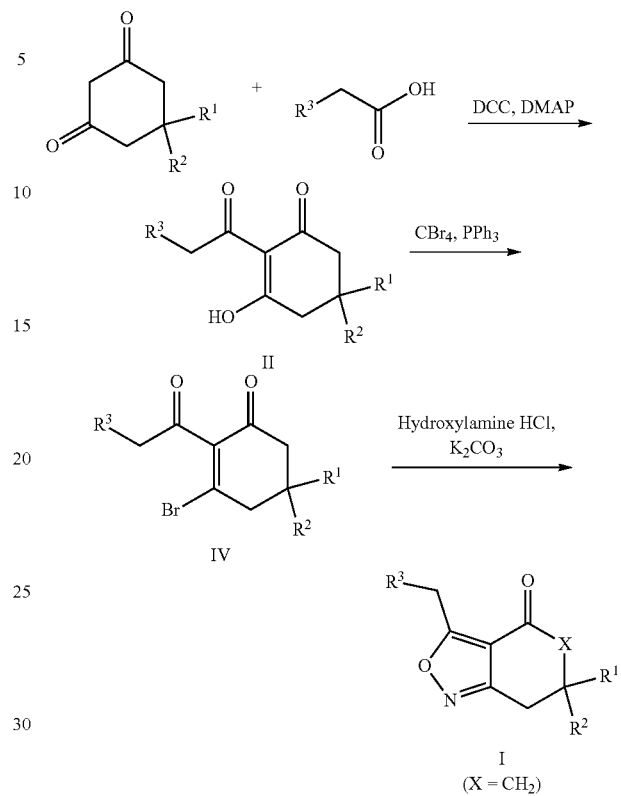

As illustrated in Scheme 1, a suitable 1,3-cyclohexanedione maybe reacted with a substituted acetic acid in the presence of a reagent such as N,N'-dicyclohexylcarbodiimide to provide II. Chlorination with oxalyl chloride provides III. Reaction of III with either hydroxylamine hydrochloride or sodium azide provides the desired compound of formula (I) wherein X=CH$_2$.

Compounds of formula (I) wherein X=CH$_2$ may also be prepared as illustrated in Scheme 2.

As illustrated in Scheme 2, a suitable 1,3-cyclohexanedione maybe reacted with a substituted acetic acid in the presence of a reagent such as N,N'-dicyclohexylcarbodiimide to provide II. Bromination with carbon tetrabromide in the presence of triphenylphosphine provides IV. Reaction of IV with hydroxylamine hydrochloride provides the desired compound of formula (I) wherein X=CH$_2$.

Compounds of formula (I) wherein X=O may be prepared as illustrated in Scheme 3.

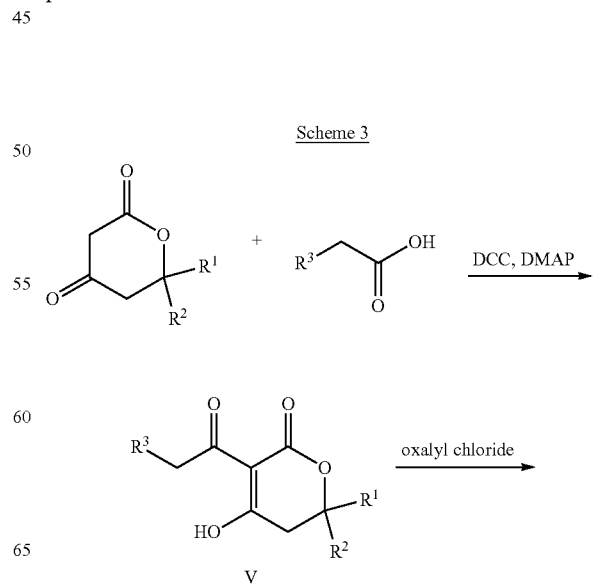

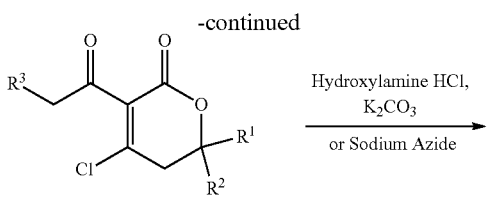

As illustrated in Scheme 3, a suitable dihydro-pyran-2,4-dione maybe reacted with a substituted acetic acid in the presence of a reagent such as N,N'-dicyclohexylcarbodiimide to provide V. Chlorination with oxalyl chloride provides VI. Reaction of VI with either hydroxylamine hydrochloride or sodium azide provides the desired compound of formula (I) wherein X=O.

SYNTHETIC EXAMPLES

Synthesis of Intermediates

Intermediate A: Synthesis of Spiro[3.5]nonane-6,8-dione

Cyclobutanone (2.0 g, 28.5 mmol) and 1-(triphenylphosphoranylidene)-2-propanone (9.1 g, 28.5 mmol) are combined and heated at 120° C. for 12 hours. The product is vacuum distilled to give 2 g of 1-cyclobutylidene-propan-2-one.

To a mixture of 2.0 g (18 mmol) of 1-cyclobutylidene-propan-2-one in 20 mL of MeOH is added 2.0 mL (18 mmol) of dimethyl malonate, followed by the addition of sodium methoxide (0.98, 18 mmol). The mixture is stirred for 2.5 hours at room temperature, and heated to reflux for 1 hour, cooled to room temperature and concentrated to provide a solid residue that is then stirred with 20 mL of 10N NaOH for 2 days. The pH is adjusted to between 2 and 3 with concentrated HCl, and the mixture is warmed to 70° C. for 3 hours, and then is cooled to room temperature and extracted three times with CH$_2$Cl$_2$. The combined extracts are washed with brine, dried (Na$_2$SO$_4$), filtered, and concentrated to provide 0.6 g of A.

Intermediate B: Synthesis of 5-(Tetrahydro-pyran-4-yl)-cyclohexane-1,3-dione

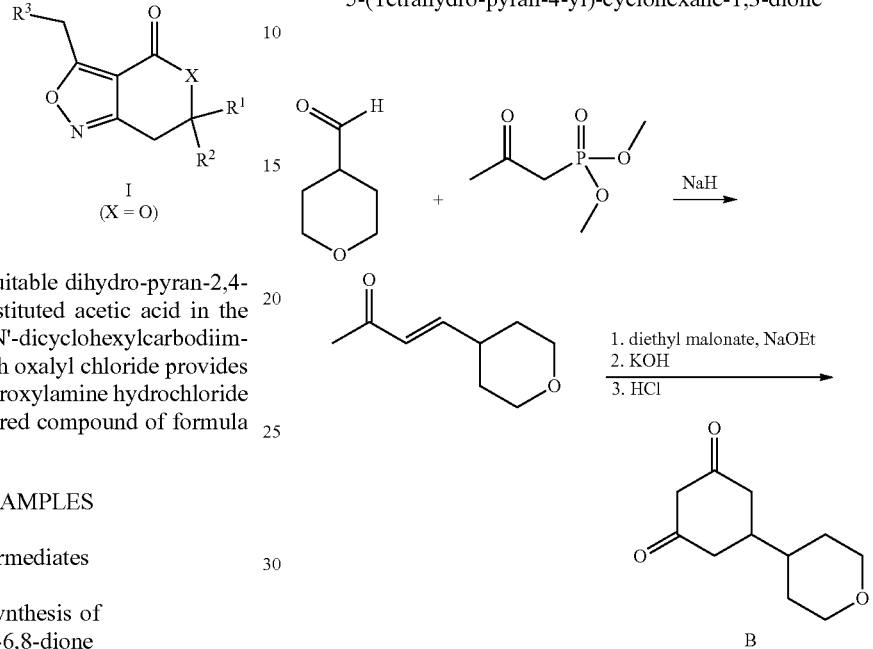

To a cooled (0° C.) suspension of 60% NaH (850 mg, 21.2 mmol) in 15 mL of DME is added dimethyl 2-oxopropylphosphonate (2.0 mL, 21.2 mmol). The mixture is warmed to room temperature as it is stirred for 30 minutes. A solution of tetrahydro-pyran-4-carbaldehye (2.3 g, 20.2 mmol) in 10 mL of DME is added drop-wise. The mixture is stirred for 30 minutes, then heated to 80° C. for 3 hours.

The reaction is quenched by the addition of saturated aq. NH$_4$Cl and is extracted with EtOAc (2×). The combined extracts are washed with water, brine, then dried over Na$_2$SO$_4$, filtered, and concentrated to provide a residue. The material is purified by silica gel chromatography eluting with EtOAc in heptanes to provide 0.76 g of 4-(tetrahydro-pyran-4-yl)-but-3-en-2-one.

To a mixture of 4-(tetrahydro-pyran-4-yl)-but-3-en-2-one (0.76 g, 4.9 mmol) in 20 mL of EtOH is added diethyl malonate (0.75 mL, 4.9 mmol), followed by the drop-wise addition of 21% NaOEt in EtOH (1.84 mL, 4.9 mmol). The mixture is stirred for 2.5 hours at room temperature, and heated to reflux for 1 hour, cooled to room temperature and concentrated to provide a solid residue that is then stirred with 20 mL of 10N NaOH for 2 days. The pH is adjusted to between 2 and 3 with concentrated HCl, and the mixture is warmed to 70° C. for 3 hours, and then is cooled to room temperature and extracted three times with CH$_2$Cl$_2$. The combined extracts are washed with brine, dried (Na$_2$SO$_4$), filtered, and concentrated to provide 0.8 g of B.

The general method used to prepare B is also used to prepare 5-cyclopropyl-methylcyclohexane-1,3-dione (C) and 5-benzyl-cyclohexane-1,3-dione (D).

Intermediate E: Synthesis of [4-(3-Methanesulfonyl-propoxy)-phenyl]-acetic acid

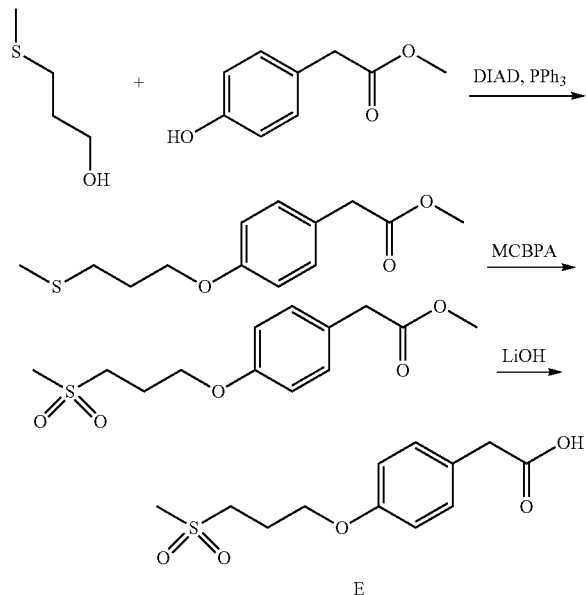

To a solution of (4-hydroxy-phenyl)-acetic acid methyl ester (2.4 g, 14.4 mmol) in 50 mL of DCM is added 3-methanesulfanyl-propan-1-ol (1.2 mL, 12 mmol), triphenylphosphine (3.8 g, 12.0 mmol), and diisopropyl azodicarboxylate (2.8 mL, 12.0 mmol) drop-wise. The reaction is stirred for 16 hours. The mixture is concentrated to dryness and the residue is purified by silica gel chromatography eluting with EtAOc in heptanes to provide 2.6 g of [4-(3-methanesulfanyl-propoxy)-phenyl]-acetic acid methyl ester.

To a solution of methanesulfanyl-propoxy)-phenyl]-acetic acid methyl ester (5.0 g, 19.7 mmol) in 100 mL of DCM is added 3-chloroperoxybenzoic acid (8.6 g, 49.1 mmol). The reaction is stirred at room temperature for 16 hours. The reaction is quenched with 1M sodium thiosulfate solution. The layers are separated, and the DCM layer is concentrated to dryness. The residue is purified by silica gel chromatography to provide 3 g of [4-(3-methanesulfonyl-propoxy)-phenyl]-acetic acid methyl ester.

To a solution of [4-(3-methanesulfonyl-propoxy)-phenyl]-acetic acid methyl ester (2.0 g, 6.9 mmol) in 18 mL of THF and 2 mL of water is added lithium hydroxide (0.83 g, 34.4 mmol). The reaction is stirred at room temperature for 16 hours. The reaction is concentrated to dryness. The residue is diluted with water and is made acidic with 1N HCl. This is extracted with EtOAc and the EtOAc layers are concentrated to dryness to provide 1.25 g of E.

The general method to prepare E is also used to prepare [4-(2-methanesulfonyl-ethoxy)-phenyl]-acetic acid (F).

Intermediate G: Synthesis of (6-Methoxy-pyridin-3-yl)-acetic acid

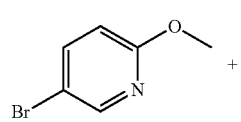

+

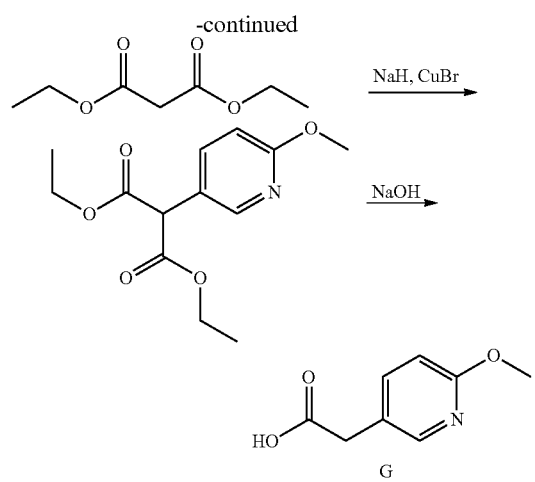

To a solution of 5-bromo-2-methoxy-pyridine (2.1 mL, 16.5 mmol), copper(I) bromide (4.7 g, 33.0 mmol) and diethylmalonate (5.0 mL, 33.0 mmol) in 20 mL of dioxane is slowly added 60% sodium hydride (1.5 g, 36.2 mmol). The resulting mixture is stirred at 100° C. for 16 hours. The mixture is filtered through a plug of diatomaceous earth to remove the solid. The filtrate is concentrated to dryness to yield an oil. The crude product is purified by silica gel chromatography eluting with EtOAc in heptane (CV: 2-10-2) to provide 0.75 g of 2-(6-methoxy-pyridin-3-yl)-malonic acid diethyl ester.

A solution of 2-(6-methoxy-pyridin-3-yl)-malonic acid diethyl ester (0.75 g, 2.8 mmol) and 2N sodium hydroxide solution (5.6 mL, 11.2 mmol) in 6 mL of THF is heated at reflux for 2.5 hours. The mixture is cooled to room temperature and acidified to pH 1 with concentrated hydrochloric acid. The resulting mixture is stirred at room temperature for 4 days. The pH is adjusted to 13 with 1N sodium hydroxide solution. The mixture is extracted with diethyl ether. The pH of the aqueous is adjusted to 4-5 with 1N hydrochloric acid. The aqueous layer is extracted with EtOAc (9×20 mL). The combined organic layer is concentrated to dryness to provide 0.20 g of G.

Intermediate H: Synthesis of (3-Cyano-4-methoxy-phenyl)-acetic acid

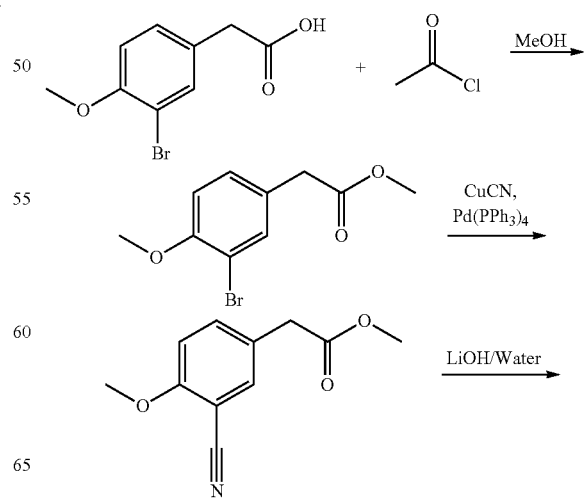

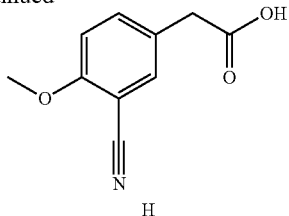

To a solution of (3-bromo-4-methoxy-phenyl)-acetic acid (2.0 g, 8.2 mmol) in 15 mL of methanol is added acetyl chloride (0.6 mL, 8.2 mmol). The solution is heated at 65° C. for 4 hours. The solvent is concentrated, and the residue is dissolved in EtAOc. This is washed with saturated sodium bicarbonate solution, dried over magnesium sulfate, filtered, and concentrated to provide 2.2 g of (3-bromo-4-methoxy-phenyl)-acetic acid methyl ester.

A solution of (3-bromo-4-methoxy-phenyl)-acetic acid methyl ester (0.5 g, 1.9 mmol), copper(I) cyanide (0.35 g, 3.8 mmol), and tetrakis(triphenylphosphine)palladium (0) (0.45 g, 0.4 mmol) in 10 mL of DMF is degassed with argon and heated in a sealed tube at 155° C. for 4 hours. Water is added and a precipitate formed. This is filtered off and discarded. The filtrate is extracted with EtOAc. This is washed with saturated sodium bicarbonate solution, dried over magnesium sulfate, filtered, and concentrated. The crude product is purified by silica gel chromatography eluting with EtOAc in heptane to provide 0.3 g of (3-cyano-4-methoxy-phenyl)-acetic acid methyl ester.

To a solution of (3-cyano-4-methoxy-phenyl)-acetic acid methyl ester (0.3 g, 1.5 mmol) in 18 mL of THF and 2 mL of water is added lithium hydroxide (0.18 g, 7.5 mmol). The reaction is stirred at room temperature for 16 hours. The reaction is concentrated to dryness. The residue is diluted with water and is made acidic with 1N HCl. This is extracted with EtOAc and the EtAOc layers are concentrated to dryness to provide 0.28 g of H.

Intermediate I: Synthesis of
(3-Cyano-4-fluoro-phenyl)-acetic acid

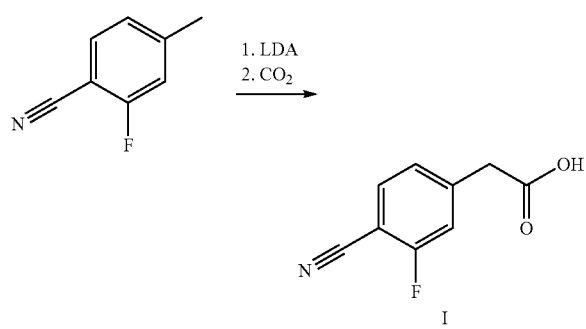

Lithium diisopropylamide solution 2.0 M in THF/heptane/ethylbenzene (20 mL, 40 mmol) is cooled to −78° C. Hexamethylphosphoramide (7.1 mL, 40 mmol) is added followed by a solution of 2-fluoro-4-methyl-benzonitrile (5.0 g, 37 mmol) in 20 mL of THF. This is kept at −78° C. for two hours. $CO_2$ is bubbled through the reaction for 1 hour. The −78° C. bath is removed. The reaction is slowly quenched with water. The reaction is diluted with EtOAc and the layers are separated. The basic water layer is made acidic with 1N HCl. This is extracted with fresh EtOAc. The second EtOAc layer is concentrated to dryness to provide 4.5 g of I.

Intermediate J: Synthesis of
4-carboxymethyl-benzoic acid tert-butyl ester

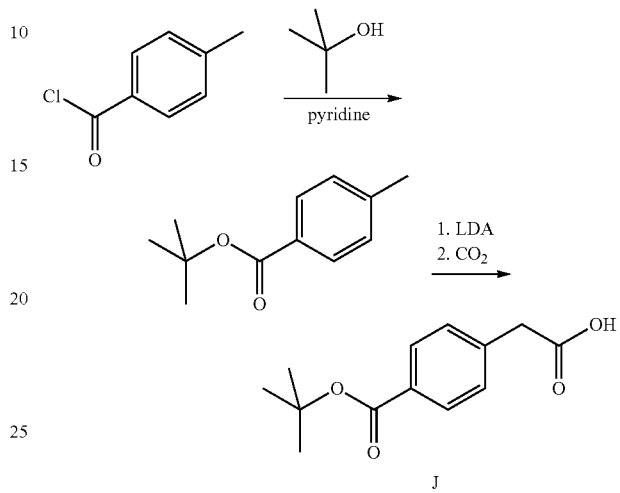

To a cooled (0° C.) mixture of pyridine (9.8 ml, 121.1 mmol) and t-butanol (9.7 ml, 103.0 mmol) is added 4-methyl-benzoyl chloride (8.0 ml, 60.56 mmol) drop-wise. The reaction is allowed to warm to room temperature and is stirred for 18 hours. The mixture is diluted with 150 mL of water and is extracted with EtOAc (3×40 mL). The combined organic fractions are washed with brine, dried over sodium sulfate, filtered, and concentrated. The crude product is purified by silica gel chromatography eluting with EtOAc in heptanes to provide 6.1 g of 4-methyl-benzoic acid tert-butyl ester.

4-Methyl-benzoic acid tert-butyl ester (6.1 g, 31.5 mmol) is converted to 5.4 g of intermediate J according to the procedure for intermediate I.

Intermediate K: Synthesis of
4-(4-Methoxycarbonylmethyl-phenoxy)-butyric acid

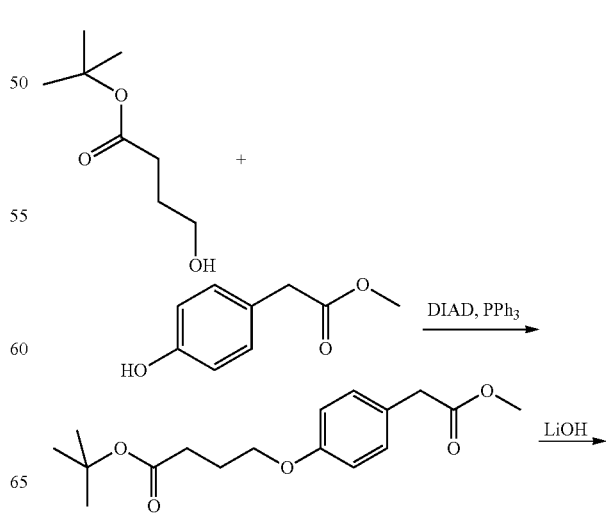

-continued

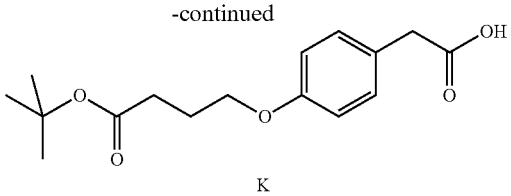

K

To a solution of (4-hydroxy-phenyl)-acetic acid methyl ester (1.2 g, 7.5 mmol) in 50 mL of DCM is added 4-Hydroxy-butyric acid tert-butyl ester (1.0 g, 6.2 mmol), triphenylphosphine (1.9 g, 7.5 mmol), and diisopropyl azodicarboxylate (1.4 mL, 7.5 mmol) drop-wise. The reaction is stirred for 16 hours. The mixture is concentrated to dryness and the residue is purified by silica gel chromatography eluting with EtOAc in heptanes to provide 1.5 g of 4-(4-Methoxycarbonylmethyl-phenoxy)-butyric acid.

To a solution of 4-(4-Methoxycarbonylmethyl-phenoxy)-butyric acid (1.5 g, 5.0 mmol) in 18 mL of THF and 2 mL of water is added lithium hydroxide (0.24 g, 10.0 mmol). The reaction is stirred at room temperature for 16 hours. The reaction is concentrated to dryness. The residue is diluted with water and is made acidic with 1N HCl. This is extracted with EtOAc and the EtAOc layers are concentrated to dryness. The residue is purified by silica gel chromatography to provide 0.62 g of K.

The general method to prepare K is also used to prepare 3-(4-carboxymethyl-phenoxy)-propionic acid tert-butyl ester (L) and [4-(2-methylsulfanyl-ethoxy)-phenyl]-acetic acid (M).

Intermediate N:
6,6-Dimethyl-dihydro-pyran-2,4-dione

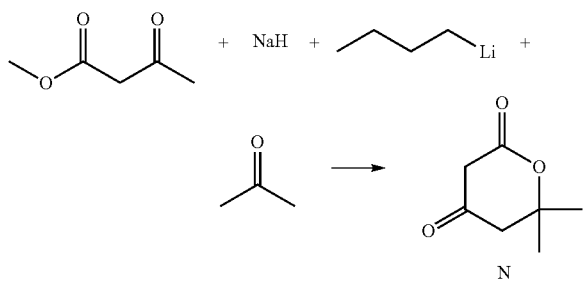

N

To a suspension of 60% sodium hydride dispersion in mineral oil (2.4 g, 60 mmol) in 100 mL of THF cooled in an ice bath is added methyl acetoacetate (5.4 mL, 50 mmol) drop-wise. The mixture is stirred at 0° C. for 30 minutes during which time all of the solids go into solution. To this is added 1.6 M butyl lithium solution in hexanes (33 mL, 53 mmol) drop-wise. The mixture is stirred for an additional 30 minutes then 4.0 mL (55 mmol) of acetone (dried over magnesium sulfate) is added. The mixture is allowed to stir at 0° C. for 2 hours. The mixture is diluted with water and is washed with ethyl acetate. The pH of the aqueous phase is adjusted to approximately pH 2 by the addition of a 2N solution of hydrochloric acid. The mixture is extracted with ethyl acetate. The combined organic phases were combined, dried over anhydrous sodium sulfate and concentrated under reduce pressure. The residue is purified by recrystallization from a heptanes/ethyl acetate mixture. The formed solid is collected by filtration and dried under reduced pressure to provide 2.1 g of N.

Synthesis of Final Compounds

Final compounds are designated by compound numbers corresponding to the compound numbers in Table 1.

Enantiomers are resolved by chiral SFC. When absolute stereochemistry is not established, by definition, the first-eluting enantiomer is referred to as enantiomer A, and the second-eluting enantiomer is referred to as enantiomer B. LCMS data are measured using the methods set forth in Table 2. LCMS data for the compounds in Table 1 are shown in Table 3. Compounds that were separated into their enantiomers are shown by separate entries in Tables 3 and 4 for enantiomer A and enantiomer B.

Example 1: Synthesis of 6,6-Spiro-cyclobutyl-3-benzyl-6,7-dihydro-5-H-benzo[c]isoxazole-4-one
(Cpd 1, Table 1)

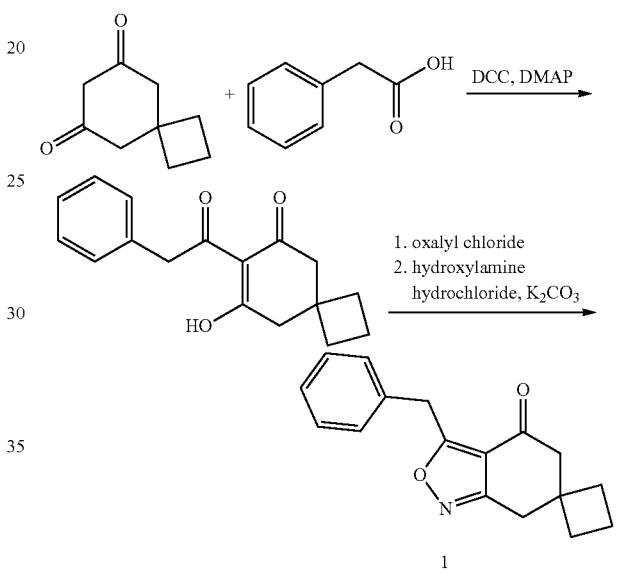

To a solution of spiro[3.5]nonane-6,8-dione (0.15 g, 1.0 mmol) and phenyl-acetic acid (134 mg, 1.0 mmol) in 5 mL of DCM is added 4-dimethylaminopyridine (0.12 g, 1.0 mmol) and 1.0 M dicyclohexylcarbodiimide solution in DCM (1.0 mL, 1.0 mmol). The reaction is stirred for 16 hours. The mixture is filtered through a pad of diatomaceous earth, washing with DCM. The filtrate is concentrated to dryness. The crude mixture is purified by silica gel chromatography eluting with EtOAc in heptane to provide 0.18 g of 8-hydroxy-7-phenylacetyl-spiro[3.5]non-7-en-6-one.

A solution of 8-hydroxy-7-phenylacetyl-spiro[3.5]non-7-en-6-one (182 mg, 0.7 mmol) in oxalyl chloride (0.6 mL, 7.0 mmol) is stirred for 16 hours. The reaction is concentrated to dryness and azeotroped with heptanes to remove the oxalyl chloride. To this residue is added a solution of potassium carbonate (370 mg, 2.8 mmol) in 3 mL of ethanol and 1 mL of water. Hydroxylamine hydrochloride (70 mg, 1.1 mmol) is added and the reaction is heated at 70° C. for 16 hours. The reaction is allowed to cool and partitioned between EtOAc and water. The layers are separated and the aqueous layer is extracted twice more with EtOAc. The organic layers are combined, washed with brine, dried over magnesium sulfate, filtered, and concentrated to dryness. The residue is purified by preparative HPLC (20-90% MeCN in water, 0.1% formic acid) to give Cpd 1.

Compounds 2, 3 and 6 through 13 in Table 1 are synthesized according to the procedure for Example 1, substituting either commercially available reagents or the appropriate intermediates described above.

Example 2: Synthesis of 4-(6-Isopropyl-4-oxo-4,5,6,7-tetrahydro-benzo[c]isoxazol-3-ylmethyl)-piperidinium hydrochloride (Cpd 14, Table 1)

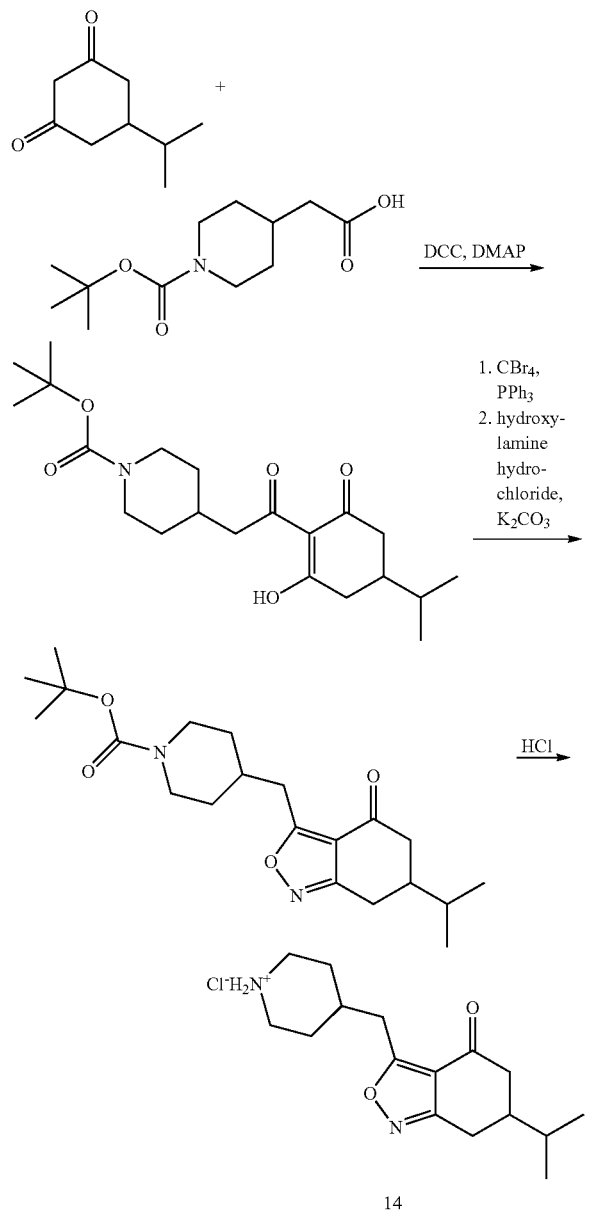

To a solution of 5-isopropyl-cyclohexane-1,3-dione (5.0 g, 32.4 mmol) and 4-carboxymethyl-piperidine-1-carboxylic acid tert-butyl ester (7.9 g, 32.4 mmol) in 20 mL of DCM is added 4-dimethylaminopyridine (4 g, 32.4 mmol) and 1.0 M dicyclohexylcarbodiimide solution in DCM (32.4 mL, 32.4 mmol). The reaction is stirred for 16 hours. The mixture is filtered through a pad of diatomaceous earth, washing with DCM. The filtrate is concentrated to dryness. The crude mixture is purified by silica gel chromatography eluting with EtOAc in heptane to give 8.6 g of 4-[2-(2-hydroxy-4-isopropyl-6-oxo-cyclohex-1-enyl)-2-oxo-ethyl]-piperidine-1-carboxylic acid tert-butyl ester.

To a solution of 4-[2-(2-hydroxy-4-isopropyl-6-oxo-cyclohex-1-enyl)-2-oxo-ethyl]-piperidine-1-carboxylic acid tert-butyl ester (8.6 g, 22.7 mmol) and triphenylphosphine (8.9 g, 34.0 mmol) in 50 mL of chloroform heated at 50° C. is added a solution of carbon tetrabromide (3.8 g, 11.3 mmol) in 25 mL of chloroform. The reaction is stirred at 500 for 4 hours. The reaction is concentrated to dryness. To this residue is added a solution of potassium carbonate (12.5 g, 90.6 mmol) in 64 mL of ethanol and 18 mL of water. Hydroxylamine hydrochloride (2.4 g, 34 mmol) is added and the reaction is heated at 70° C. for 16 hours. The reaction is allowed to cool and partitioned between EtOAc and water. The layers are separated and the aqueous layer is extracted twice more with EtOAc. The organic layers are combined, washed with brine, dried over magnesium sulfate, filtered, and concentrated to dryness. The crude mixture is purified by silica gel chromatography eluting with EtOAc in heptane to give 2.6 g of 4-(6-isopropyl-4-methylene-4,5,6,7-tetrahydro-benzo[c]isoxazol-3-ylmethyl)-piperidine-1-carboxylic acid tert-butyl ester.

To a solution of 4-(6-isopropyl-4-methylene-4,5,6,7-tetrahydro-benzo[c]isoxazol-3-ylmethyl)-piperidine-1-carboxylic acid tert-butyl ester (2.6 g, 7.0 mmol) in 10 mL of methanol is added 5 mL of 4.0 M HCl in dioxane solution. The reaction is stirred at room temperature for 16 hours. The reaction is concentrated to dryness to provide 2.3 g of Cpd 14.

Example 3: Synthesis of the enantiomers of 3-(1-Acetyl-piperidin-4-ylmethyl)-6-isopropyl-6,7-dihydro-5H-benzo[c]isoxazol-4-one (Cpd 15, Table 1)

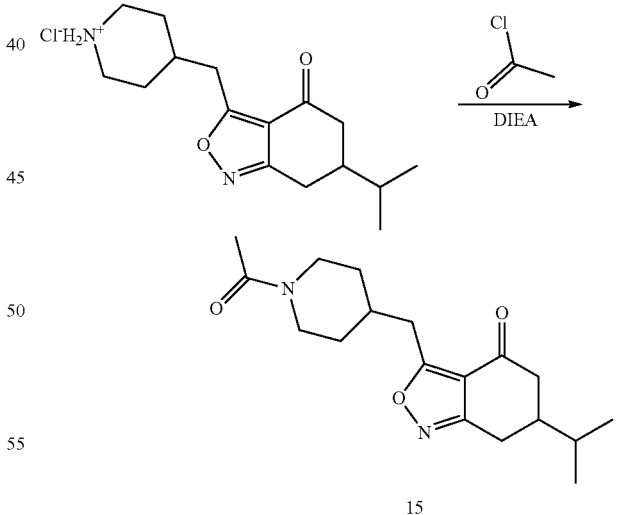

To a solution of 4-(6-isopropyl-4-oxo-4,5,6,7-tetrahydro-benzo[c]isoxazol-3-ylmethyl)-piperidinium hydrochloride (0.7 g, 2.2 mmol) in 10 mL of DMF is added N,N-diisopropylethylamine (1.2 mL, 6.6 mmol) and acetyl chloride (0.24 mL, 3.4 mmol). The reaction is stirred at room temperature for 16 hours. The reaction is partitioned between EtOAc and water. The layers are separated and the aqueous layer is extracted twice more with EtOAc.

The organic layers are combined, washed with brine, dried over magnesium sulfate, filtered, and concentrated to dryness. The crude mixture is purified by silica gel chromatography eluting with EtOAc in heptane to give 0.45 g of the racemic material.

Chiral resolution (RegisPack SFC Investigator, 7% EtOH (1% DEA) in $CO_2$ at 15 mL/min, 180 Bar, 40° C.) of 156 mg of the racemic material gives 38 mg of enantiomer A and 26 mg of enantiomer B.

Compounds 16 and 17 in Table 1 are synthesized according to the procedures outlined in Example 2 and 3, substituting either commercially available reagents or the appropriate intermediates described above.

Example 4: Synthesis of 6-Isopropyl-3-[1-(2-methoxy-acetyl)-piperidin-4-ylmethyl]-6,7-dihydro-5H-benzo[c]isoxazol-4-one (Cpd 18, Table 1)

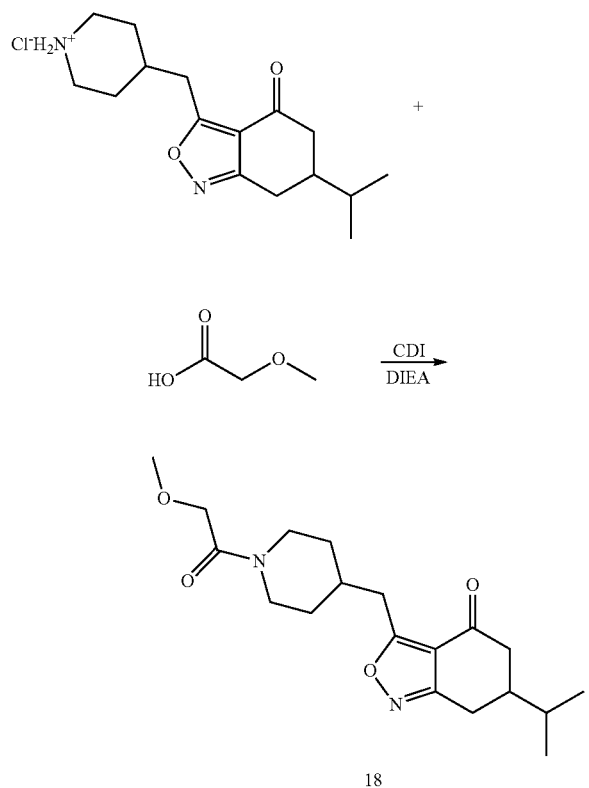

To a solution of 4-(6-isopropyl-4-oxo-4,5,6,7-tetrahydro-benzo[c]isoxazol-3-ylmethyl)-piperidinium hydrochloride (80 mg, 0.3 mmol) in 1.5 mL of DMF is added 1,1-carbonyldiimidazole (45 mg, 0.3 mmol). The reaction is stirred at room temperature for 30 minutes when N,N-diisopropylethylamine (0.13 mL, 0.9 mmol) and methoxy-acetic acid (21 µL, 0.3 mmol) are added. The reaction is stirred at room temperature for 16 hours. The crude reaction mixture is purified by preparative HPLC (20-90% MeCN in water, 0.1% formic acid) to give Cpd 18.

Compounds 19 and 20 in Table 1 are synthesized according to the procedure outlined in Example 4, substituting either commercially available reagents or the appropriate intermediates described above.

Example 5: Synthesis of 4-(6-Isopropyl-4-oxo-4,5,6,7-tetrahydro-benzo[c]isoxazol-3-ylmethyl)-piperidine-1-carboxylic acid amide (Cpd 21, Table 1)

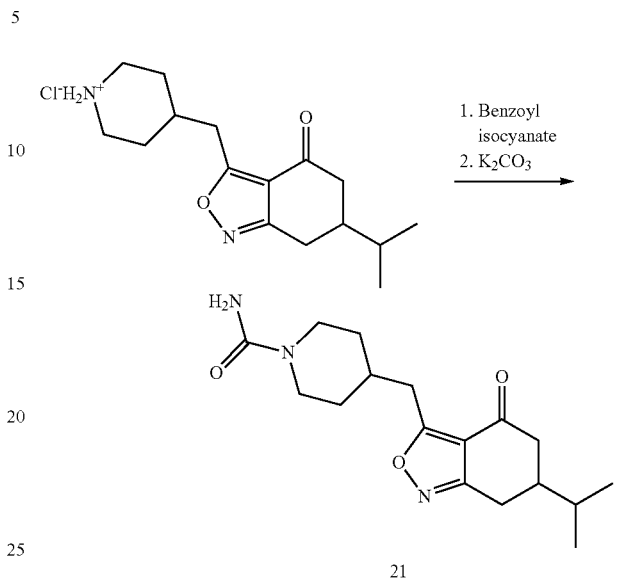

To a solution of 4-(6-isopropyl-4-oxo-4,5,6,7-tetrahydro-benzo[c]isoxazol-3-ylmethyl)-piperidinium hydrochloride (150 mg, 0.5 mmol) in 5 mL of DCM was added benzoyl isocyanate (117 mg, 0.7 mmol) and N,N-diisopropylethylamine (0.17 mL, 1.0 mmol). The reaction was stirred at room temperature for 16 hours. The reaction is concentrated to dryness. The residue is dissolved in a mixture of 5 mL of ethanol and 0.5 mL of water. Potassium carbonate (110 mg, 0.8 mmol) is added and the reaction is heated at 80° C. for 16 hours. The reaction is partitioned between EtOAc and water. The layers are separated and the aqueous layer is extracted twice more with EtOAc. The organic layers are combined, washed with brine, dried over magnesium sulfate, filtered, and concentrated to dryness. The crude reaction mixture is purified by preparative HPLC (10-90% MeCN in water, 0.1% formic acid) to give 40 mg of Cpd 21.

Compound 22 in Table 1 is synthesized according to the procedure outlined in Example 5, substituting either commercially available reagents or the appropriate intermediates described above.

Example 6: Synthesis of 4-(6,6-Dimethyl-4-oxo-4,5,6,7-tetrahydro-benzo[c]isoxazol-3-ylmethyl)-benzonitrile (Cpd 23, Table 1)

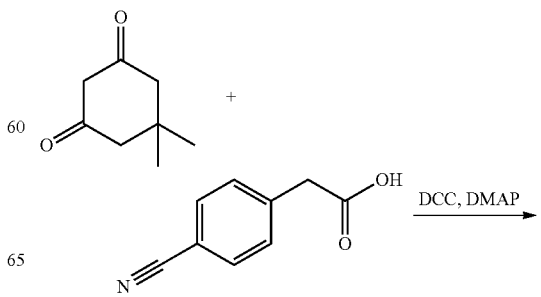

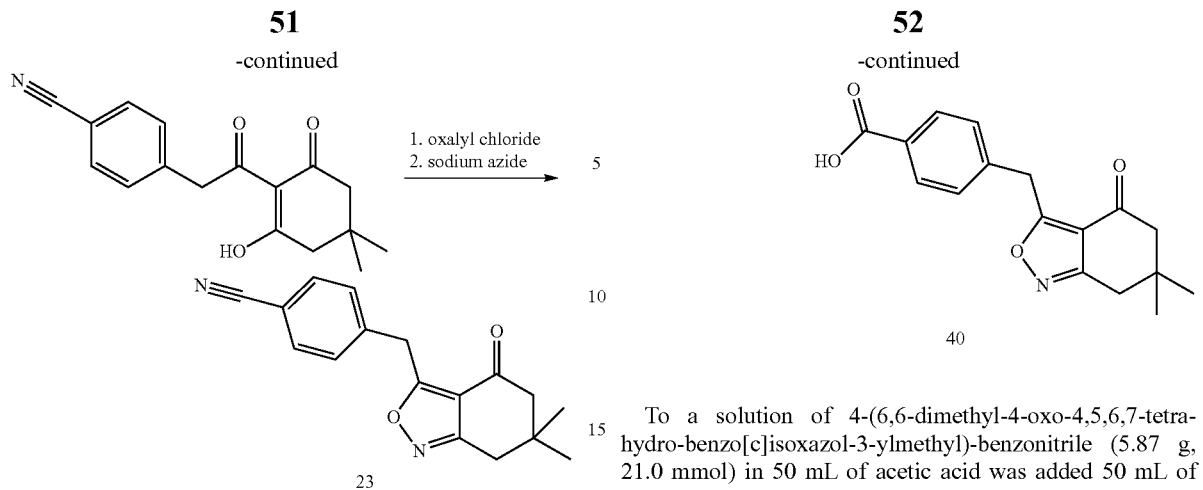

To a solution of 5,5-dimethyl-cyclohexane-1,3-dione (8.7 g, 62.0 mmol) and (4-cyano-phenyl)-acetic acid (10 g, 62.0 mmol) in 200 mL of DCM cooled in an ice bath is added 4-dimethylaminopyridine (3.8 g, 31.0 mmol) and 1.0 M dicyclohexylcarbodiimide solution in DCM (62.0 mL, 62.0 mmol). The reaction is allowed to warm to room temperature and is stirred for 16 hours. The mixture is filtered through a pad of diatomaceous earth, washing with DCM. The filtrate is concentrated to dryness. The crude mixture is purified by silica gel chromatography eluting with EtOAc in heptane to provide 10.4 g of 4-[2-(2-hydroxy-4,4-dimethyl-6-oxo-cyclohex-1-enyl)-2-oxo-ethyl]-benzonitrile.

A solution of 4-[2-(2-hydroxy-4,4-dimethyl-6-oxo-cyclohex-1-enyl)-2-oxo-ethyl]-benzonitrile (10.4 g, 36.7 mmol) in oxalyl chloride (31.0 mL, 367.0 mmol) is stirred at room temperature for 16 hours. The reaction is concentrated to dryness and azeotroped with heptanes to remove the oxalyl chloride. This residue is diluted with 50 mL of DMF and sodium azide (3.65 g, 56.2 mmol) is added in portion-wise. The reaction is stirred at room temperature for 1 hour. The reaction is partitioned between EtOAc and water. The layers are separated and the aqueous layer is extracted twice more with EtOAc. The organic layers are combined, washed with brine, dried over magnesium sulfate, filtered, and concentrated to dryness. The residue is purified by preparative silica gel chromatography eluting with EtOAc in heptane to provide 3.5 g of Cpd 23.

Compounds 24 through 31, 33 through 39 and 47 through 50 in Table 1 are synthesized according to the procedure outlined in Example 6, substituting either commercially available reagents or the appropriate intermediates described above. Compound 39 is separated into its enantiomers via chiral SFC.

Example 7: Synthesis of 4-(6,6-Dimethyl-4-oxo-4,5,6,7-tetrahydro-benzo[c]isoxazol-3-ylmethyl)-benzoic acid (Cpd 40, Table 1)

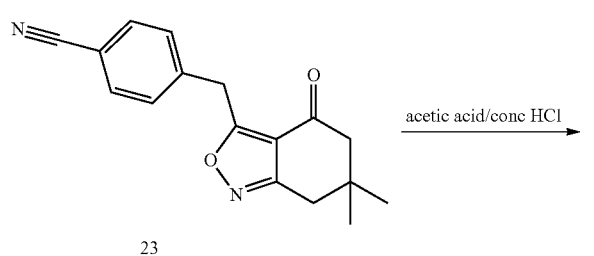

To a solution of 4-(6,6-dimethyl-4-oxo-4,5,6,7-tetrahydro-benzo[c]isoxazol-3-ylmethyl)-benzonitrile (5.87 g, 21.0 mmol) in 50 mL of acetic acid was added 50 mL of concentrated hydrochloric acid. The reaction was heated at 95° C. for 16 hours. The reaction is allowed to cool, and water was added. A precipitate forms, which is filtered off and dried to give 5.7 g of Cpd 40.

Compounds 41 through 44 in Table 1 are synthesized according to the procedure outlined in Example 7.

Example 8: Synthesis of 4-(6-Cyclopropylmethyl-4-oxo-4,5,6,7-tetrahydro-benzo[c]isoxazol-3-ylmethyl)-benzoic acid (Cpd 45, Table 1)

4-(6-Cyclopropylmethyl-4-oxo-4,5,6,7-tetrahydro-benzo[c]isoxazol-3-ylmethyl)-benzoic acid tert-butyl ester is synthesized from 4-carboxymethyl-benzoic acid tert-butyl ester and 5-cyclopropylmethyl-cyclohexane-1,3-dione according to the procedure outlined in Example 6.

To a solution of 4-(6-cyclopropylmethyl-4-oxo-4,5,6,7-tetrahydro-benzo[c]isoxazol-3-ylmethyl)-benzoic acid tert-butyl ester (267.0 mg; 0.7 mmol) in 4 mL of dichloromethane is added trifluoro-acetic acid (1.0 ml; 13.5 mmol) and the reaction is stirred at room temperature for 1 hour. The reaction mixture is concentrated and the residue is partitioned between water (25 mL) and EtOAc (15 mL). The fractions are separated and the aqueous fraction is extracted with EtOAc (2×15 mL). The combined organic fractions are washed with brine (1×20 mL), dried over sodium sulfate, filtered, and concentrated to afford 227 mg of Cpd 45.

Example 9: Synthesis of 3-[4-((R)-3-Hydroxy-pyrrolidine-1-carbonyl)-benzyl]-6,6-dimethyl-6,7-dihydro-5H-benzo[c]isoxazol-4-one (Cpd 46 Table 1)

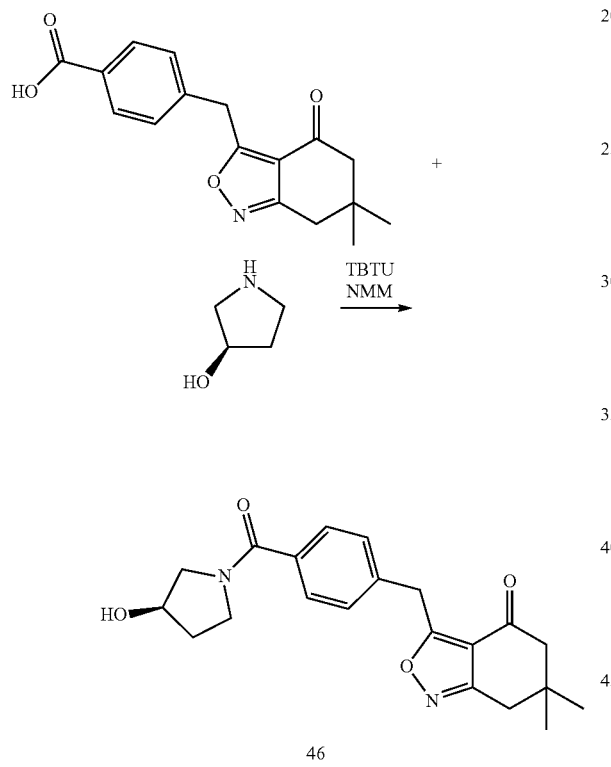

To a solution of 4-(6,6-dimethyl-4-oxo-4,5,6,7-tetrahydro-benzo[c]isoxazol-3-ylmethyl)-benzoic acid (100.0 mg; 0.3 mmol) in 1 mL of DMF is sequentially added N-methylmorpholine (0.07 mL, 0.7 mmol), O-(Benzotriazol-1-yl)-N,N,N',N'-tetramethyluronium tetrafluoroborate (134.0 mg; 0.4 mmol), and (R)-pyrrolidin-3-ol (29 mg; 0.3 mmol). The reaction is stirred for 18 hours at room temperature. The crude reaction mixture is purified by preparative HPLC (10-90% MeCN in water, 0.1% formic acid) to give Cpd 46.

Compounds 51 through 73 in Table 1 are synthesized according to the procedure outlined in Example 9, substituting either commercially available reagents or the appropriate intermediates described above.

Example 10: Synthesis of 4-(6-Methyl-4-oxo-4,5,6,7-tetrahydro-benzo[c]isoxazol-3-ylmethyl)-benzamide (Cpd 74, Table 1)

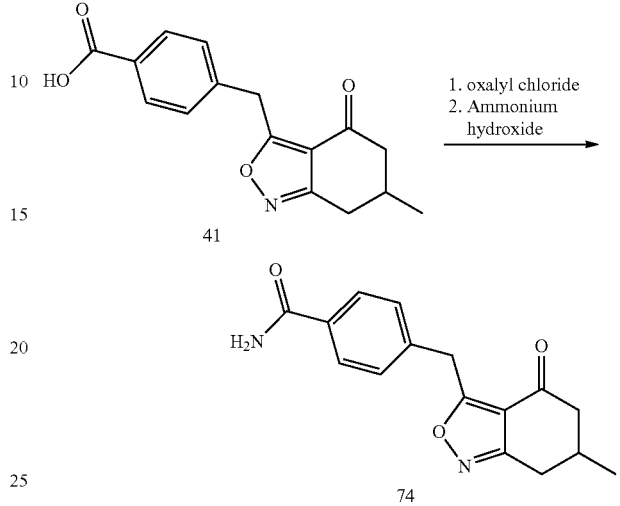

To a solution of 41 (200 mg, 0.7 mmol) in 5 mL of DCM is added oxalyl chloride (0.06 mL, 0.7 mmol) and several drops of DMF. The reaction is stirred at room temperature for 2 hours when 0.4 mL of ammonium hydroxide solution is added. The reaction is stirred for an additional 2 h and concentrated to dryness. The crude product is purified by preparative HPLC (10-90% MeCN in water, 0.1% formic acid) to give Cpd 74.

Compounds 75 through 77 in Table 1 are synthesized according to the procedure outlined in Example 10, substituting either commercially available reagents or the appropriate intermediates described above.

Example 11: Synthesis of 4-[4-(6,6-Dimethyl-4-oxo-4,5,6,7-tetrahydro-benzo[c]isoxazol-3-ylmethyl)-phenoxy]-butyramide (Cpd 78, Table 1

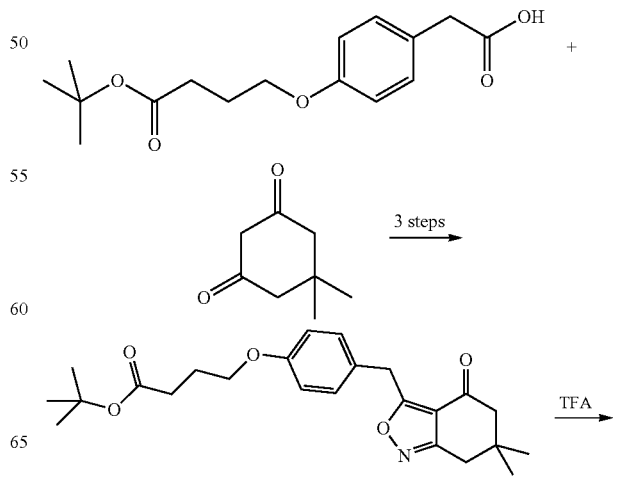

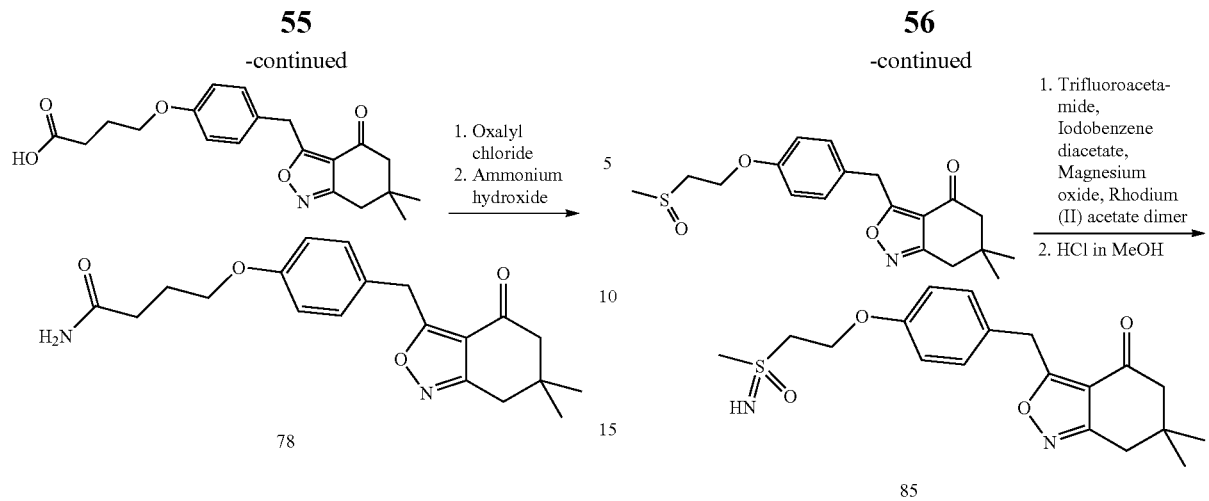

4-[4-(6,6-Dimethyl-4-oxo-4,5,6,7-tetrahydro-benzo[c]isoxazol-3-ylmethyl)-phenoxy]-butyric acid tert-butyl ester is synthesized from 4-(4-carboxymethyl-phenoxy)-butyric acid tert-butyl ester and 5,5-dimethyl-cyclohexane-1,3-dione according to the procedure outlined in Example 6.

To a solution of 4-[4-(6,6-dimethyl-4-oxo-4,5,6,7-tetrahydro-benzo[c]isoxazol-3-ylmethyl)-phenoxy]-butyric acid tert-butyl ester (400 mg, 1.0 mmol) in 10 mL of DCM is added trifluoro acetic acid (0.72 mL, 10 mmol). The reaction is stirred at room temperature for 16 hours. The reaction is concentrated to dryness to give 340 mg of 4-[4-(6,6-dimethyl-4-oxo-4,5,6,7-tetrahydro-benzo[c]isoxazol-3-ylmethyl)-phenoxy]-butyric acid.

4-[4-(6,6-Dimethyl-4-oxo-4,5,6,7-tetrahydro-benzo[c]isoxazol-3-ylmethyl)-phenoxy]-butyramide (Cpd 78) is synthesized from 4-[4-(6,6-dimethyl-4-oxo-4,5,6,7-tetrahydro-benzo[c]isoxazol-3-ylmethyl)-phenoxy]-butyric acid according to the procedure outlined in Example 10.

Compounds 79 through 84 in Table 1 are synthesized according to the procedure outlined in Example 11, substituting either commercially available reagents or the appropriate intermediates described above.

Example 12: Synthesis of 3-[4-(2-Methanesulfoximine-ethoxy)-benzyl]-6,6-dimethyl-6,7-dihydro-5H-benzo[c]isoxazol-4-one (Cpd 85, Table 1)

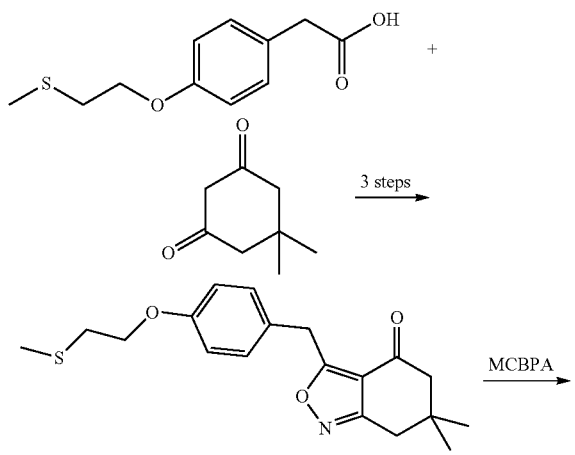

6,6-Dimethyl-3-[4-(2-methylsulfanyl-ethoxy)-benzyl]-6,7-dihydro-5H-benzo[c]isoxazol-4-one is synthesized from [4-(2-methylsulfanyl-ethoxy)-phenyl]-acetic acid and 5,5-dimethyl-cyclohexane-1,3-dione according to the procedure outlined in Example 6.

To a solution of 6,6-dimethyl-3-[4-(2-methylsulfanyl-ethoxy)-benzyl]-6,7-dihydro-5H-benzo[c]isoxazol-4-on (1.9 g, 5.5 mmol) in 50 mL of DCM cooled in an ice bath is added meta-chloroperoxybenzoic acid (1.2 g, 5.5 mmol) portion-wise. The reaction is stirred for 1 hour.

Saturated sodium sulfite solution is added. The layers are separated, and the DCM layer is washed with 1N NaOH solution. The organic layer is concentrated to dryness. The crude product is purified by silica gel chromatography eluting with MeOH in DCM to give 1.3 of 3-[4-(2-Methanesulfinyl-ethoxy)-benzyl]-6,6-dimethyl-6,7-dihydro-5H-benzo[c]isoxazol-4-one.

To a solution of 3-[4-(2-methanesulfinyl-ethoxy)-benzyl]-6,6-dimethyl-6,7-dihydro-5H-benzo[c]isoxazol-4-one (0.3 g, 0.8 mmol) in 8 mL of DCM is added trifluoroacetamide (0.18 g, 1.7 mmol), iodobenzene diacetate (0.40 g, 1.2 mmol), magnesium oxide (0.13 g, 3.3 mmol), and rhodium (II) acetate dimer, (0.026 g, 0.1 mmol). The reaction is stirred at room temperature for 3 days. The reaction is filtered and concentrated to dryness. The crude material is dissolved in 3 mL of 1.25 M HCl in methanol. This is stirred at room temperature overnight. The reaction is concentrated to dryness and purified on a silica gel column eluting with MeOH in DCM to give 20.0 mg of Cpd 85.

Example 13: Synthesis of 4-(6,6-Dimethyl-4-oxo-6,7-dihydro-4H-pyrano[4,3-c]isoxazol-3-ylmethyl)-benzonitrile (Cpd 87, Table 1)

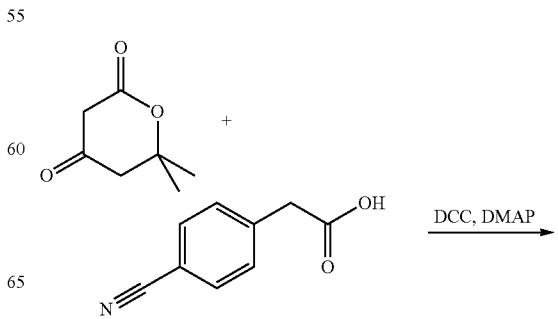

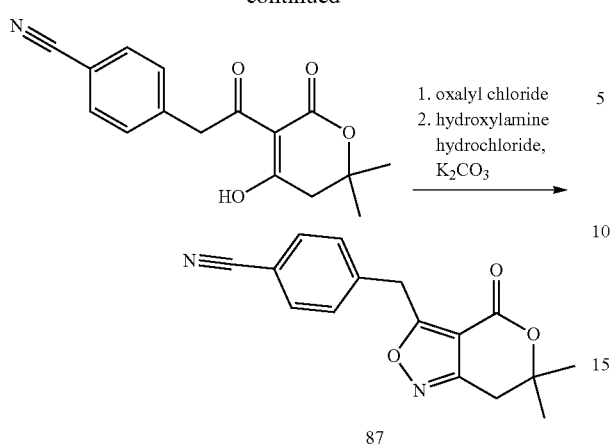

6,6-Dimethyl-dihydro-pyran-2,4-dione and phenylacetic acid are converted to 87 in three steps according to the procedure outlined in Example 1. Compounds 88 and 89 are prepared in a similar fashion.

Example 14: Synthesis of 3-[4-(3-Methanesulfonyl-propoxy)-benzyl]-6,6-dimethyl-6,7-dihydro-pyrano[4,3-c]isoxazol-4-one (Cpd 90, Table 1)

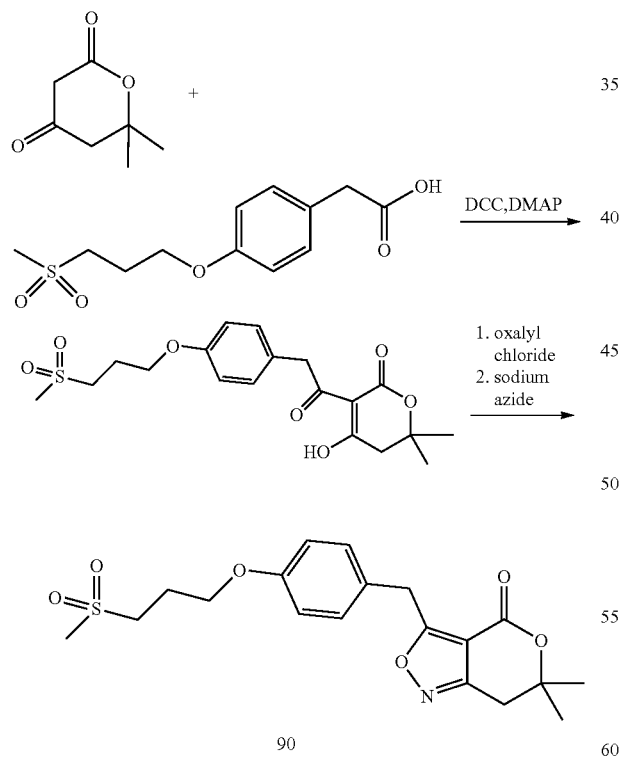

6,6-Dimethyl-dihydro-pyran-2,4-dione and [4-(3-Methanesulfonyl-propoxy)-phenyl]-acetic acid are converted to 90 in three steps according to the procedure outlined in example 6. Compounds 91 and 92 are prepared in a similar fashion.

Example 15: Synthesis of 3-[4-((R)-3-Hydroxy-pyrrolidine-1-carbonyl)-benzyl]-6,6-dimethyl-6,7-dihydro-pyrano[4,3-c]isoxazol-4-one (Cpd 93, Table 1)

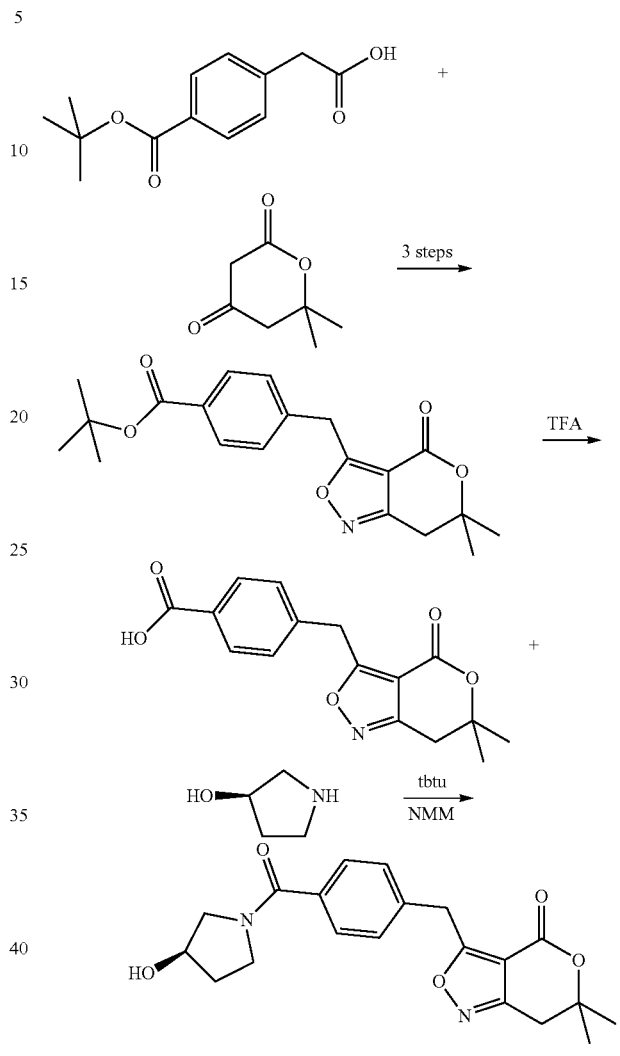

6,6-Dimethyl-dihydro-pyran-2,4-dione and 4-Carboxymethyl-benzoic acid tert-butyl ester are converted to 4-(6,6-Dimethyl-4-oxo-6,7-dihydro-4H-pyrano[4,3-c]isoxazol-3-ylmethyl)-benzoic acid tert-butyl ester in three steps according to the procedure outlined in Example 6.

To a solution of the 4-(6,6-dimethyl-4-oxo-6,7-dihydro-4H-pyrano[4,3-c]isoxazol-3-ylmethyl)-benzoic acid tert-butyl ester (200 mg, 0.6 mmol) in 5 mL of DCM is added trifluoroacetic acid (0.43 mL, 6.0 mmol). The reaction is stirred at room temperature for 2 hours. The reaction is concentrated to dryness. The residue is purified on a silica gel column eluting with 2-8% MeOH in DCM to provide 130 mg of 4-(6,6-dimethyl-4-oxo-6,7-dihydro-4H-pyrano[4,3-c]isoxazol-3-ylmethyl)-benzoic acid.

4-(6,6-Dimethyl-4-oxo-6,7-dihydro-4H-pyrano[4,3-c]isoxazol-3-ylmethyl)-benzoic acid and (R)-pyrrolidin-3-ol are converted to compound 93 according to the procedure outlined in Example 9.

Compounds 94 through 97 in Table 1 are synthesized according to the procedure outlined in Example 15, substituting either commercially available reagents or the appropriate intermediates described above.

LCMS Data for compounds in Table 1 are shown in Table 3, and are measured using the methods set forth in the following Table 2.

TABLE 2

LCMS Methods

| Method | Mobile Phase A | Mobile Phase B | Gradient | | | Flow (mL/min.) | Column |
|---|---|---|---|---|---|---|---|
| A | 0.1% Formic Acid in Water | 0.1% Formic Acid in Acetonitrile | Time (min) | % A | % B | 0.5 | Thermo Scientific, Aquasil C18, 50 × 2.1 mm, 5 μ |
| | | | 0 | 90.0 | 10.0 | | |
| | | | 0.5 | 90.0 | 10.0 | | |
| | | | 1.5 | 1.0 | 99.0 | | |
| | | | 2.5 | 1.0 | 99.0 | | |
| | | | 3.3 | 90.0 | 10.0 | | |
| | | | 4.0 | 90.0 | 10.0 | | |
| B | 95% Water 5% Acetonitrile + 0.05% Formic Acid | Acetonitrile + 0.05% Formic Acid | 90% A to 100% B in 1.19 minutes, hold at 100% B to 1.70 minutes | | | 0.8 | BEH 2.1 × 50 mm C18, 1.7 μm particle diameter |
| C | 95% Water 5% Acetonitrile + 0.05% Formic Acid | Acetonitrile + 0.05% Formic Acid | 90% A to 100% B in 4.45 minutes, hold at 100% B to 4.58 minutes | | | 0.8 | BEH 2.1 × 50 mm C18, 1.7 μm particle diameter |

TABLE 3

LC-MS Data

| Cpd | Mass Found | Retention Time (Min) | LCMS Method | Cpd | Mass Found | Retention Time (Min) | LCMS Method |
|---|---|---|---|---|---|---|---|
| 1 | 268.1 | 1.05 | B | 49 | 454.2 | 0.96 | B |
| 2 | 282.3 | 3.14 | A | 50 | 404.2 | 2.02 | C |
| 3 | 314.3 | 3.01 | A | 51 | 325.3 | 0.83 | B |
| 6 | 234.3 | 3.12 | A | 52 | 353.4 | 3.01 | A |
| 7 | 278.3 | 3.05 | A | 53 | 431.4 | 2.81 | A |
| 8 | 342.2 | 1.02 | B | 54 | 406.1 | 0.70 | B |
| 9 | 334.2 | 2.87 | A | 55 | 371.3 | 2.70 | A |
| 10 | 287.3 | 3.01 | A | 56 | 371.4 | 2.95 | A |
| 11 | 281.2 | 0.95 | B | 57 | 431.1 | 0.82 | B |
| 12 | 337.0 | 2.04 | A | 58 | 357.4 | 2.89 | A |
| 13 | 274.3 | 0.35 | A | 59 | 357.4 | 2.79 | A |
| 14 | 277.3 | 2.47 | A | 60 | 383.3 | 2.73 | A |
| 15A | 319.2 | 1.65 | C | 61 | 405.3 | 2.64 | A |
| 15B | 319.2 | 1.65 | C | 62 | 382.4 | 2.75 | A |
| 16 | 317.2 | 2.81 | A | 63 | 395.3 | 1.96 | A |
| 17 | 305.3 | 2.85 | A | 64 | 419.4 | 2.70 | A |
| 18 | 349.4 | 2.95 | A | 65 | 369.4 | 2.78 | A |
| 19 | 335.2 | 0.83 | B | 66 | 382.3 | 2.63 | A |
| 20 | 397.4 | 2.86 | A | 67 | 385.4 | 2.78 | A |
| 21 | 320.3 | 2.91 | A | 68 | 352.3 | 2.73 | A |
| 22 | 318.3 | 2.83 | A | 69 | 369.4 | 2.69 | A |
| 23 | 281.2 | 0.94 | B | 70 | 411.3 | 2.88 | A |
| 24 | 418.1 | 0.94 | B | 71 | 357.3 | 2.65 | A |
| 25 | 382.2 | 3.24 | A | 72 | 383.3 | 2.70 | A |
| 26 | 318.3 | 3.18 | A | 73 | 357.3 | 2.66 | A |
| 27 | 392.1 | 0.87 | B | 74 | 285.2 | 2.75 | A |
| 28 | 343.3 | 3.10 | A | 75 | 299.3 | 2.64 | A |
| 29 | 378.3 | 2.80 | A | 76 | 313.2 | 2.90 | A |
| 30 | 307.1 | 1.01 | B | 77 | 311.1 | 0.73 | B |
| 31 | 274.3 | 3.05 | A | 78 | 357.4 | 2.86 | A |
| 33 | 334.1 | 3.22 | A | 79 | 385.4 | 3.04 | A |
| 34 | 311.3 | 2.93 | A | 80 | 357.1 | 0.78 | B |
| 35 | 327.2 | 2.90 | A | 81 | 343.1 | 0.74 | B |
| 36 | 267.3 | 2.94 | A | 82 | 371.0 | 0.85 | B |
| 37 | 299.0 | 0.92 | B | 83 | 413.2 | 0.75 | B |
| 38 | 293.3 | 3.00 | A | 84 | 427.3 | 0.76 | B |
| 39A | 295.1 | 0.97 | B | 85 | 377.3 | 0.73 | B |
| 39B | 295.1 | 0.97 | B | 87 | 283.2 | 0.77 | B |
| 40 | 300.3 | 2.84 | A | 88 | 276.1 | 0.94 | B |
| 41 | 286.3 | 2.84 | A | 89 | 288.2 | 0.96 | B |
| 42 | 362.1 | 0.92 | B | 90 | 394.1 | 0.77 | B |
| 43 | 312.1 | 0.74 | B | 91 | 380.1 | 0.75 | B |
| 44 | 314.0 | 0.89 | B | 92 | 266.1 | 0.71 | B |
| 45 | 326.2 | 0.96 | B | 93 | 371.2 | 0.59 | B |
| 46 | 369.4 | 2.78 | A | 94 | 407.1 | 0.63 | B |
| 47 | 406.3 | 2.94 | A | 95 | 301.1 | 0.59 | B |
| 48 | 378.2 | 2.91 | A | 96 | 359.2 | 0.60 | B |
| | | | | 97 | 398.2 | 0.61 | B |

Assessment of Biological Activity

Preparation of Cynomolgus Adrenal Mitochondria

The aldosterone synthase and cortisol synthase inhibition assays employ cynomolgus adrenal gland mitochondria as the source of aldosterone synthase (CYP11B2) and cortisol synthase (CYP11B1). Mitochondria are prepared from frozen cynomolgus monkey adrenal glands according to Method A described in by J. D. McGarry et al. (Biochem. J., 1983, 214, 21-28), with a final resuspension in the AT buffer described in R. Yamaguchi et al. (Cell Death and Differentiation, 2007, 14, 616-624), frozen as aliquots in liquid nitrogen and stored at −80° C. until use. Activity of CYP11B2 and CYP11B1 in these preparations is defined as the amount of enzyme that generates 1 pmol of product in one hour under the conditions described.

Inhibition of Aldosterone Synthase

The compounds of the invention may be evaluated for aldosterone synthase inhibition by the following assay:

Assays are performed in 96-well format in a final volume of 60 L/well, containing 100 mM potassium phosphate, pH 7.4, 1% (v/v) DMSO, and additionally, 2 μM of corticosterone and 50 units of CYP11B2 activity. Reactions are started by the addition of NADPH to 1 mM and allowed to proceed for 90 minutes at 37° C. Reactions are terminated by the addition of 60 μL of MeCN containing an internal standard for mass spectrometry. One hundred microliters are then transferred to a glass filter plate and centrifuged at 570×g for 5 minutes and the filtrate is collected. Reaction product aldosterone is quantified by mass spectrometry. To determine the assay blank value (0% activity), NADPH is omitted from some reactions.

Dose dependent inhibition is quantified by the inclusion of compound at various concentrations. Maximum activity (100%) is defined by reactions containing NADPH, but without compound. Activities at each concentration are expressed as a percentage of the maximum activity (y-axis) and plotted against concentration of compound (x-axis) and the concentration corresponding to 50% activity ($IC_{50}$) determined using the XLFit curve-fitting program using a 4-parameter logistic model.

Inhibition of Cortisol Synthesis

Assays are performed as for aldosterone synthase except for the use of 150 units of CYP11B1, 11-deoxycortisol as substrate and cortisol measured as product.

Representative compounds of the present invention were tested for activity in the above assays. Preferred compounds have an aldosterone synthase (CYP11B2) $IC_{50}$<1,000 nM and more preferred compounds have an aldosterone synthase (CYP11B2) $IC_{50}$<100 nM in this assay. As examples, data for representative compounds from Table 1 are shown in Table 4. Data for individual enantiomers are indicated by separate entries for enantiomers A and B.

TABLE 4

Biological Data

| Cpd | CYP11B2 Inhibition $IC_{50}$ (nM) | CYP11B1 Inhibition $IC_{50}$ (nM) | Cpd | CYP11B2 Inhibition $IC_{50}$ (nM) | CYP11B1 Inhibition $IC_{50}$ (nM) |
|---|---|---|---|---|---|
| 1 | 7.2 | 1100 | 49 | 150 | 1100 |
| 2 | 11 | 5000 | 50 | 72 | 580 |
| 3 | 17 | 590 | 51 | 21 | 3700 |
| 6 | 27 | 21000 | 52 | 32 | 14000 |
| 7 | 33 | 20000 | 53 | 42 | 6700 |
| 8 | 78 | >100000 | 54 | 58 | 2500 |
| 9 | 84 | 3700 | 55 | 68 | 5400 |
| 10 | 110 | 7700 | 56 | 69 | 11000 |
| 11 | 140 | 9300 | 57 | 80 | 2600 |
| 12 | 180 | 51000 | 58 | 89 | 3400 |
| 13 | 190 | 22000 | 59 | 92 | 11000 |
| 14 | 2400 | >30000 | 60 | 94 | 5900 |
| 15A | 22 | 2800 | 61 | 91 | 7400 |
| 15B | 110 | 18000 | 62 | 98 | 20000 |
| 16 | 47 | 3900 | 63 | 110 | 4100 |
| 17 | 690 | 24000 | 64 | 110 | 9300 |
| 18 | 89 | 2800 | 65 | 110 | 7600 |
| 19 | 200 | 9900 | 66 | 120 | 5000 |
| 20 | 410 | 14000 | 67 | 120 | 7300 |
| 21 | 330 | 23000 | 68 | 160 | 7800 |
| 22 | 57 | 3500 | 69 | 160 | 13000 |
| 23 | 69 | 74000 | 70 | 160 | 11000 |
| 24 | 17 | 1300 | 71 | 170 | 20000 |
| 25 | 29 | 2800 | 72 | 180 | 5900 |
| 26 | 49 | 2300 | 73 | 230 | 23000 |
| 27 | 59 | 3400 | 74 | 82 | 3000 |
| 28 | 65 | 4900 | 75 | 100 | 15000 |
| 29 | 73 | 7400 | 76 | 25 | 530 |
| 30 | 74 | 14000 | 77 | 12 | 130 |
| 31 | 84 | 7400 | 78 | 24 | 3300 |
| 33 | 92 | 4100 | 79 | 23 | 7800 |
| 34 | 120 | 25000 | 80 | 29 | 1800 |
| 35 | 160 | 5200 | 81 | 35 | 2500 |
| 36 | 200 | 7600 | 82 | 44 | 4000 |
| 37 | 74 | 11000 | 83 | 69 | 2700 |
| 38 | 55 | 1000 | 84 | 69 | 6900 |

TABLE 4-continued

Biological Data

| Cpd | CYP11B2 Inhibition $IC_{50}$ (nM) | CYP11B1 Inhibition $IC_{50}$ (nM) | Cpd | CYP11B2 Inhibition $IC_{50}$ (nM) | CYP11B1 Inhibition $IC_{50}$ (nM) |
|---|---|---|---|---|---|
| 39A | 230 | 8300 | 85 | 56 | 6500 |
| 39B | 120 | 3400 | 87 | 220 | 77000 |
| 40 | >1000 | >100000 | 88 | 190 | 25000 |
| 41 | 660 | 20000 | 89 | 27 | 9800 |
| 42 | 180 | >100000 | 90 | 16 | 4600 |
| 43 | — | — | 91 | 120 | 21000 |
| 44 | — | — | 92 | 340 | 69000 |
| 45 | 420 | 64000 | 93 | 73 | 2600 |
| 46 | 130 | 5800 | 94 | 42 | 4300 |
| 47 | 20 | 130 | 95 | 71 | 16000 |
| 48 | 46 | 670 | 96 | 73 | 10000 |
|  |  |  | 97 | 170 | 11000 |

Methods of Therapeutic Use

In accordance with the invention, there are provided novel methods of using the compounds of formula (I). The compounds disclosed herein effectively inhibit aldosterone synthase. The inhibition of aldosterone synthase is an attractive means for preventing and treating a variety of diseases or conditions that can be alleviated by lowering levels of aldosterone. Thus, the compounds are useful for the treatment of diseases and conditions as described in the Background section, including the following conditions and diseases:

Diabetic kidney disease including diabetic nephropathy;

Non-diabetic kidney disease including glomerulosclerosis, glomerulonephritis, IGA nephropathy, nephritic syndrome and focal segmental glomerulosclerosis (FSGS);

Cardiovascular diseases including hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism;

Adrenal hyperplasia and primary and secondary hyperaldosteronism.

These disorders have been well characterized in man, but also exist with a similar etiology in other mammals, and can be treated by pharmaceutical compositions of the present invention.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, Pharmaceutical Dosage Forms and Drug Delivery Systems, 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors.

For instance, specific dosage and treatment regimens will depend on factors such as the patient's general health profile, the severity and course of the patient's disorder or disposition thereto, and the judgment of the treating physician.

What is claimed is:
1. A compound of formula I

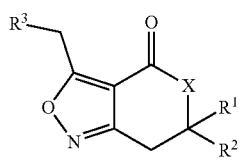

wherein:
X is —CH$_2$— or —O—;
R$^1$ and R$^2$ are independently selected from H, C$_{1-3}$alkyl, —CH$_2$-cyclopropyl, benzyl, and tetrahydropyran-4-yl, provided that R$^1$ and R$^2$ are not both H; or
R$^1$ and R$^2$ may together form a spiro cyclobutyl ring;
R$^3$ is selected from
phenyl, optionally substituted with one to two groups independently selected from the group consisting of —SO$_2$C$_{1-3}$alkyl, —CN, -halogen, —C(O)OH, —C(O)NR$^4$R$^5$, —O(CH$_2$)$_{2-3}$C(O)N(R$^6$)(R$^7$), —O(CH$_2$)$_2$S(O)(NH)CH$_3$, and —O(CH$_2$)$_{2-3}$ SO$_2$CH$_3$;
wherein if R$^1$ and/or R$^2$ is H or C$_{1-3}$alkyl, the phenyl substitution is not optional; and wherein
if the phenyl is substituted with at least one of the groups listed above, or if R$^1$ and/or R$^2$ is not H or C$_{1-3}$alkyl, or if X is O, the phenyl may also be optionally substituted with C$_{1-3}$alkyl, or —OC$_{1-3}$alkyl;
cyclopropyl;
2,3-dihydro-benzo[1,4]dioxin-6-yl;
a 4H-benzo[1,4]oxazin-3-one-6-yl;
tetrahydropyran-4-yl;
piperidin-4-yl, optionally substituted with a group selected from —C(O)CH$_3$, —C(O)CH$_2$OCH$_3$, —C(O)CH$_2$OH, —C(O)CH$_2$SO$_2$CH$_3$ and —C(O)NH$_2$;
pyridyl, optionally substituted with —OCH$_3$;
R$^4$ and R$^5$ are independently selected from H and C$_{1-3}$alkyl, wherein the C$_{1-3}$alkyl is optionally substituted with one to two groups independently selected from —SO$_2$CH$_3$, —SO$_2$NH$_2$, OH, —OCH$_3$, —CN and a spiro C$_{3-5}$cycloalkyl group; or
R$^4$ and R$^5$ together with the N they are attached to may form a pyrrolidine, piperidine or piperazine ring, optionally substituted with one to two groups independently selected from —OH, —SO$_2$CH$_3$, —CH$_3$ and oxo;
R$^6$ and R$^7$ are independently selected from H and CH$_3$; or together with the N they are attached to may form a pyrrolidine ring, optionally substituted with —OH;
or pharmaceutically acceptable salt thereof.

2. The compound of formula I according to claim 1, wherein
R$^1$ and R$^2$ are independently selected from H, C$_{1-3}$alkyl and —CH$_2$-cyclopropyl, provided that
R$^1$ and R$^2$ are not both H; or
R$^1$ and R$^2$ may together form a spiro cyclobutyl ring;
R$^3$ is selected from
phenyl, substituted with one to two groups independently selected from —SO$_2$CH$_3$, —CN, —F, —I, —C(O)NR$^4$R$^5$, —O(CH$_2$)$_{2-3}$C(O)N(R$^6$)(R$^7$), —O(CH$_2$)$_2$S(O)(NH)CH$_3$, and —O(CH$_2$)$_{2-3}$ SO$_2$CH$_3$; and
piperidin-4-yl, substituted on the nitrogen with a group selected from —C(O)CH$_3$, —C(O)CH$_2$OCH$_3$, —C(O)CH$_2$OH, —C(O)CH$_2$SO$_2$CH$_3$ and —C(O)NH$_2$;
R$^4$ and R$^5$ are independently selected from H and C$_{1-3}$alkyl, wherein the C$_{1-3}$alkyl is optionally substituted with one to two groups independently selected from —SO$_2$CH$_3$, —SO$_2$NH$_2$, OH, —OCH$_3$, —CN and a spiro C$_{3-5}$cycloalkyl group; or
R$^4$ and R$^5$ together with the N they are attached to may form a pyrrolidine ring, optionally substituted a group selected from —OH and —SO$_2$CH$_3$;
R$^6$ and R$^7$ are independently selected from H and CH$_3$; or together with the N they are attached to may form a pyrrolidine ring, optionally substituted with —OH;
or pharmaceutically acceptable salt thereof.

3. The compound of the formula I according to claim 1, wherein
R$^1$ and R$^2$ are independently selected from H and C$_{1-3}$alkyl, provided that R$^1$ and R$^2$ are not both H; or
R$^1$ and R$^2$ may together form a spiro cyclobutyl ring;
R$^3$ is selected from
phenyl, substituted with one to two groups independently selected from —SO$_2$CH$_3$, —CN, —F, —C(O)NR$^4$R$^5$ and —O(CH$_2$)$_{2-3}$SO$_2$CH$_3$; and piperidin-4-yl, substituted on the nitrogen with —C(O)CH$_3$;

R$^4$ and R$^5$ are independently selected from H, and C$_{1-3}$alkyl, wherein the C$_{1-3}$alkyl is optionally substituted with one to two groups independently selected from —SO$_2$CH$_3$, —SO$_2$NH$_2$ and OH; or R$^5$ and R$^5$ together with the N they are attached to may form a pyrrolidine ring, substituted with a —OH;

or pharmaceutically acceptable salt thereof.

4. The compound of the formula I according to claim 1, wherein

X is CH$_2$;

or pharmaceutically acceptable salt thereof.

5. The compound of the formula I according to claim 1, wherein

X is O;

or pharmaceutically acceptable salt thereof.

6. The compound according to claim 1, selected from the group consisting of

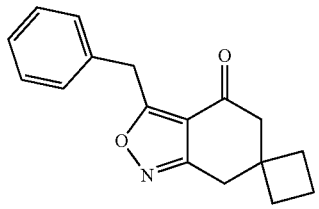 [SMILES: O=C1CC2(CCC2)Cc2noc(Cc3ccccc3)c21]

1

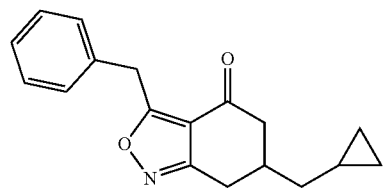 [SMILES: O=C1CC(CC2CC2)Cc2noc(Cc3ccccc3)c21]

2

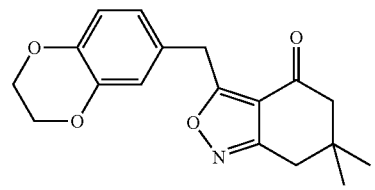 [SMILES: CC1(C)CC(=O)c2c(noc2Cc2ccc3c(c2)OCCO3)C1]

3

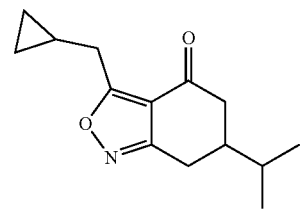 [SMILES: CC(C)C1CC(=O)c2c(noc2CC2CC2)C1]

6

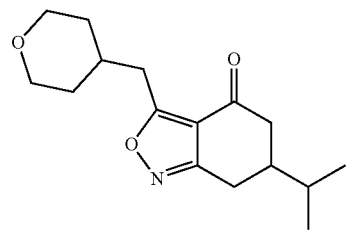 [SMILES: CC(C)C1CC(=O)c2c(noc2CC2CCOCC2)C1]

7

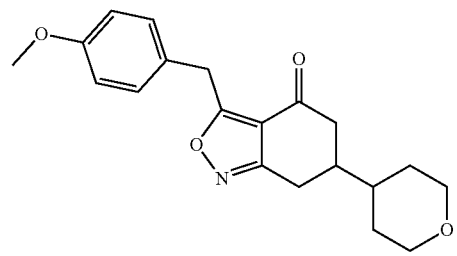 [SMILES: COc1ccc(Cc2onc3c2C(=O)CC(C2CCOCC2)C3)cc1]

8

-continued
| | |
|---|---|
| 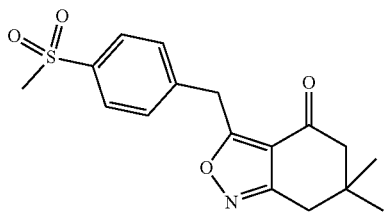 [SMILES: CC1(C)CC(=O)c2c(noc2Cc2ccc(S(C)(=O)=O)cc2)C1] | 9 |
| 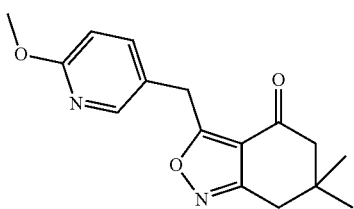 | 10 |
| 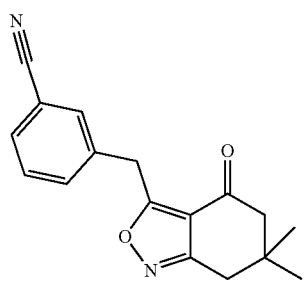 [SMILES: CC1(C)CC(=O)c2c(noc2Cc2cccc(C#N)c2)C1] | 11 |
| 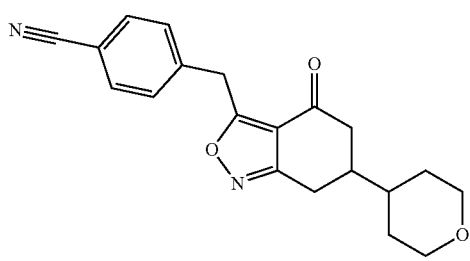 [SMILES: N#Cc1ccc(Cc2onc3c2C(=O)CC(C2CCOCC2)C3)cc1] | 12 |
| 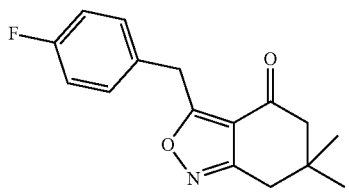 [SMILES: CC1(C)CC(=O)c2c(noc2Cc2ccc(F)cc2)C1] | 13 |
| 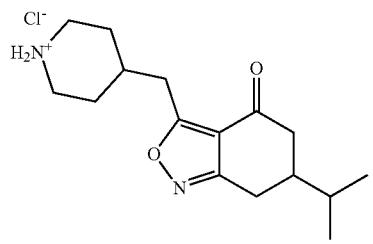 [SMILES: [Cl-] ; CC(C)C1CC(=O)c2c(noc2CC2CC[NH2+]CC2)C1] | 14 |

-continued
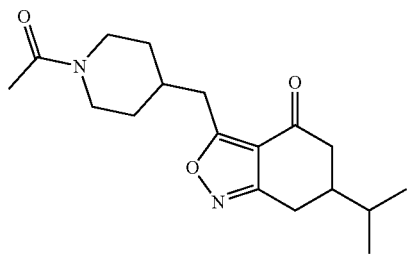 [SMILES: CC(=O)N1CCC(Cc2onc3c2C(=O)CC(C(C)C)C3)CC1]
15
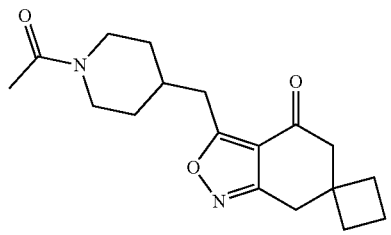 [SMILES: CC(=O)N1CCC(Cc2onc3c2C(=O)CC2(CCC2)C3)CC1]
16
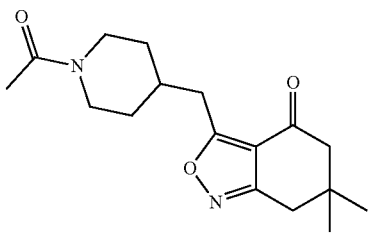 [SMILES: CC(=O)N1CCC(Cc2onc3c2C(=O)CC(C)(C)C3)CC1]
17
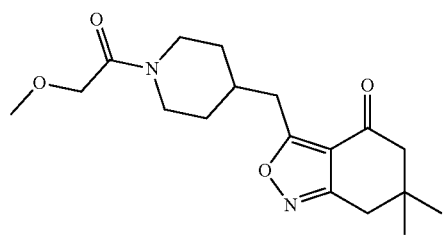
18
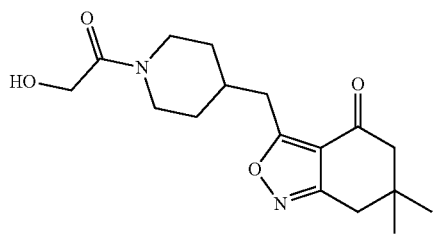 [SMILES: CC1(C)CC(=O)c2c(noc2CC2CCN(C(=O)CO)CC2)C1]
19
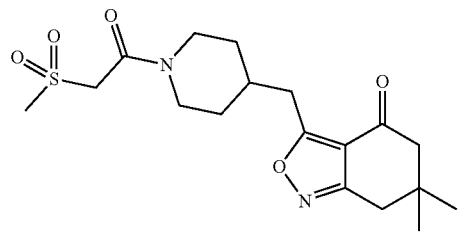 [SMILES: CC1(C)CC(=O)c2c(noc2CC2CCN(C(=O)CS(C)(=O)=O)CC2)C1]
20

21
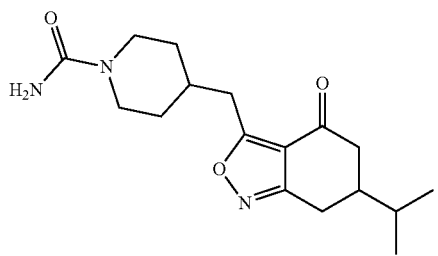 [SMILES: CC(C)C1CC(=O)c2c(noc2CC2CCN(C(N)=O)CC2)C1]
22
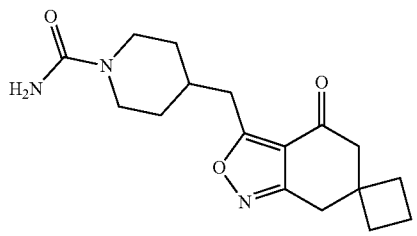 [SMILES: NC(=O)N1CCC(Cc2onc3c2C(=O)CC2(CCC2)C3)CC1]
23
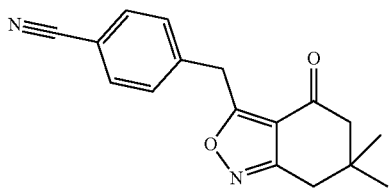 [SMILES: CC1(C)CC(=O)c2c(noc2Cc2ccc(C#N)cc2)C1]
24
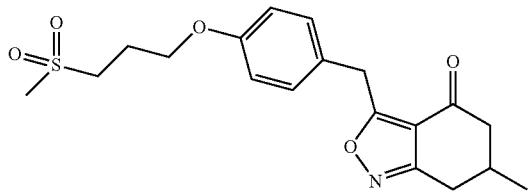 [SMILES: CC1CC(=O)c2c(noc2Cc2ccc(OCCCS(C)(=O)=O)cc2)C1]
25
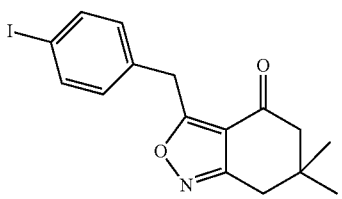 [SMILES: CC1(C)CC(=O)c2c(noc2Cc2ccc(I)cc2)C1]
26
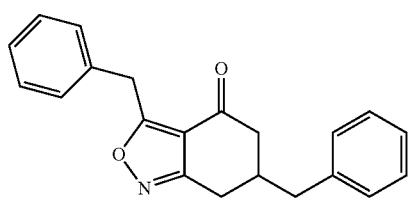 [SMILES: O=C1CC(Cc2ccccc2)Cc2noc(Cc3ccccc3)c21]
27
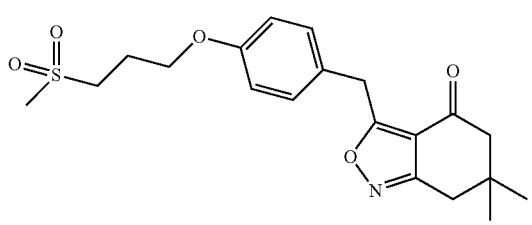 [SMILES: CC1(C)CC(=O)c2c(noc2Cc2ccc(OCCCS(C)(=O)=O)cc2)C1]

-continued
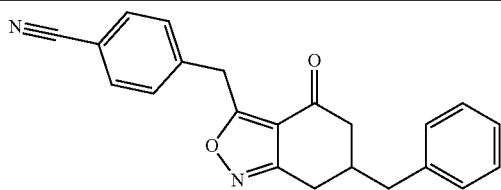
28
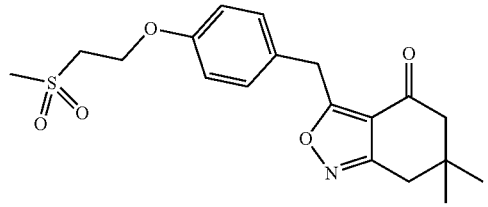
29
30
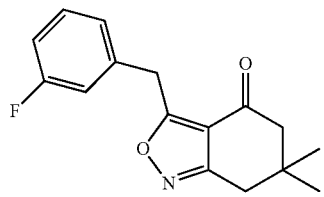 [SMILES: CC1(C)CC(=O)c2c(noc2Cc2cccc(F)c2)C1]
31
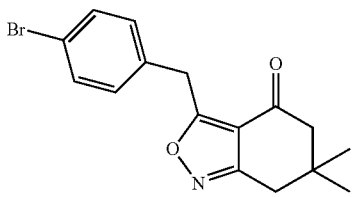
33
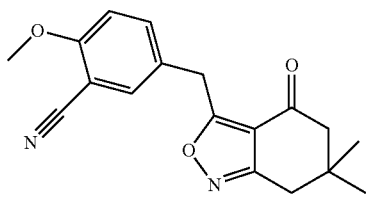
34
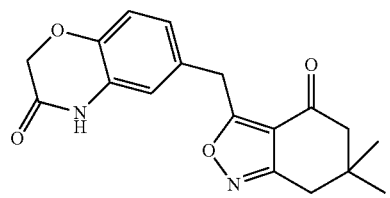 [SMILES: CC1(C)CC(=O)c2c(noc2Cc2ccc3c(c2)NC(=O)CO3)C1]
35
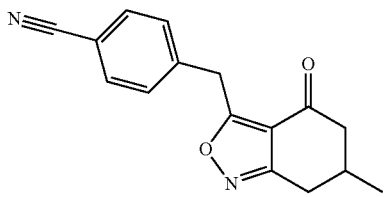 [SMILES: CC1CC(=O)c2c(noc2Cc2ccc(C#N)cc2)C1]
36

-continued
| | |
|---|---|
| 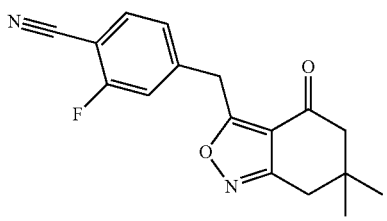 [SMILES: CC1(C)CC(=O)c2c(noc2Cc2ccc(C#N)c(F)c2)C1] | 37 |
| 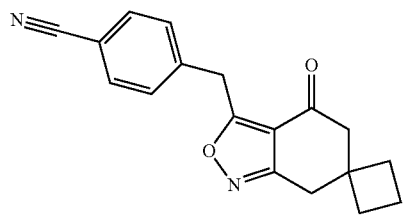 [SMILES: N#Cc1ccc(Cc2onc3c2C(=O)CC2(CCC2)C3)cc1] | 38 |
| 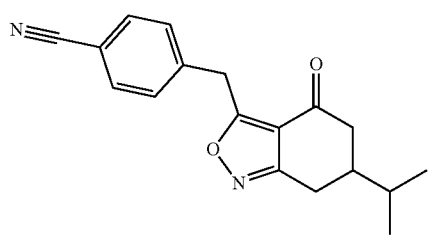 [SMILES: CC(C)C1CC(=O)c2c(noc2Cc2ccc(C#N)cc2)C1] | 39 |
| 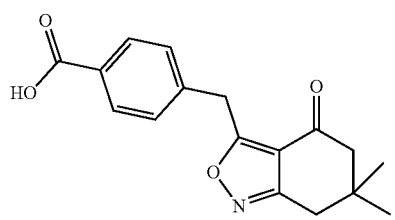 [SMILES: CC1(C)CC(=O)c2c(noc2Cc2ccc(C(=O)O)cc2)C1] | 40 |
| 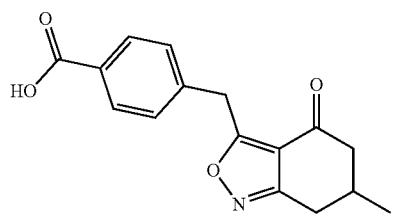 [SMILES: CC1CC(=O)c2c(noc2Cc2ccc(C(=O)O)cc2)C1] | 41 |
| 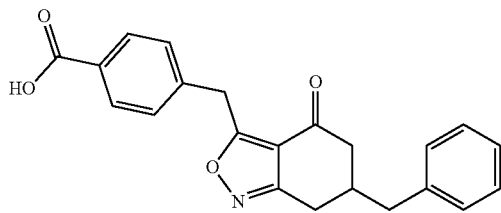 [SMILES: O=C(O)c1ccc(Cc2onc3c2C(=O)CC(Cc2ccccc2)C3)cc1] | 42 |
| 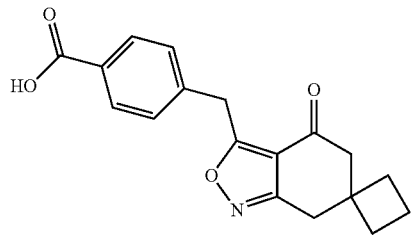 [SMILES: O=C(O)c1ccc(Cc2onc3c2C(=O)CC2(CCC2)C3)cc1] | 43 |

| | |
|---|---|
| 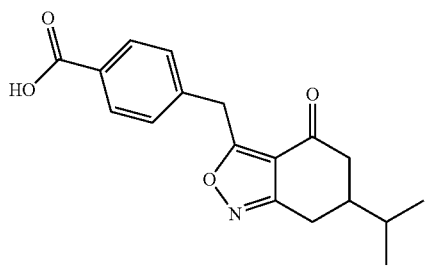 [SMILES: CC(C)C1CC(=O)c2c(noc2Cc2ccc(C(=O)O)cc2)C1] | 44 |
| 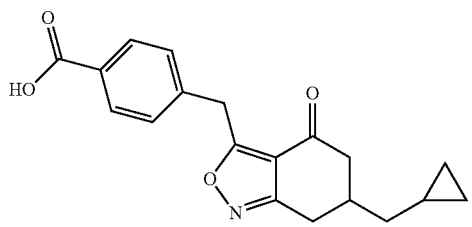 [SMILES: O=C(O)c1ccc(Cc2onc3c2C(=O)CC(CC2CC2)C3)cc1] | 45 |
| 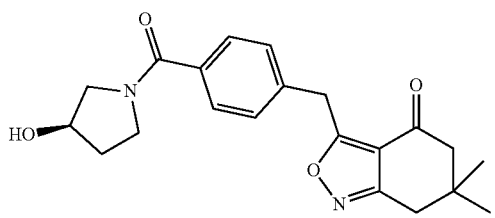 [SMILES: CC1(C)CC(=O)c2c(noc2Cc2ccc(C(=O)N3CC[C@@H](O)C3)cc2)C1] | 46 |
| 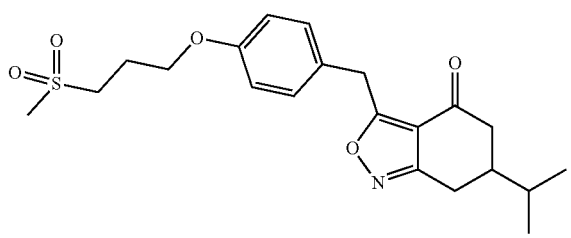 [SMILES: CC(C)C1CC(=O)c2c(noc2Cc2ccc(OCCCS(C)(=O)=O)cc2)C1] | 47 |
| 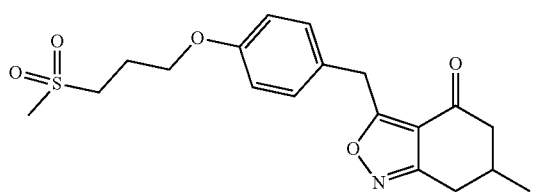 [SMILES: CC1CC(=O)c2c(noc2Cc2ccc(OCCCS(C)(=O)=O)cc2)C1] | 48 |
| 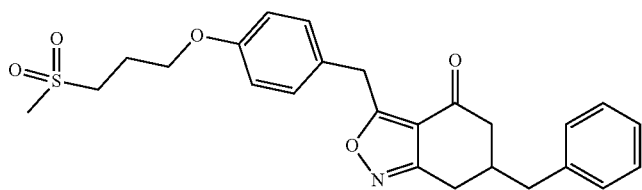 [SMILES: CS(=O)(=O)CCCOc1ccc(Cc2onc3c2C(=O)CC(Cc2ccccc2)C3)cc1] | 49 |
| 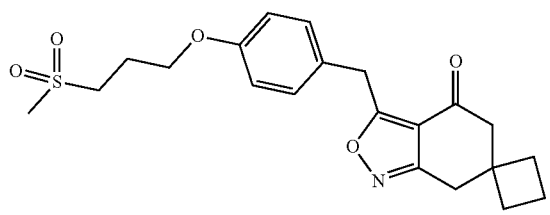 [SMILES: CS(=O)(=O)CCCOc1ccc(Cc2onc3c2C(=O)CC2(CCC2)C3)cc1] | 50 |

-continued
| | |
|---|---|
| 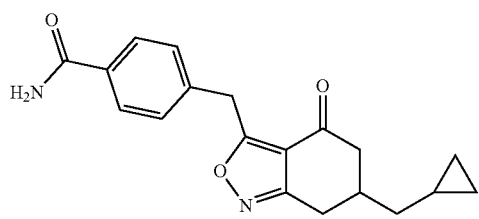 [SMILES: NC(=O)c1ccc(Cc2onc3c2C(=O)CC(CC2CC2)C3)cc1] | 51 |
| 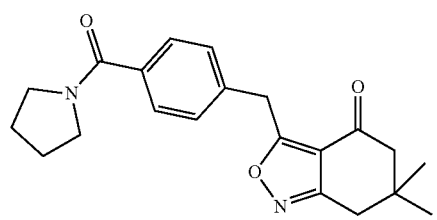 [SMILES: CC1(C)CC(=O)c2c(noc2Cc2ccc(C(=O)N3CCCC3)cc2)C1] | 52 |
| 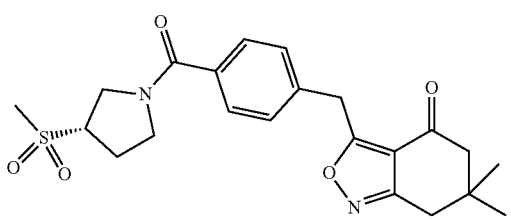 [SMILES: CC1(C)CC(=O)c2c(noc2Cc2ccc(C(=O)N3CC[C@H](S(C)(=O)=O)C3)cc2)C1] | 53 |
| 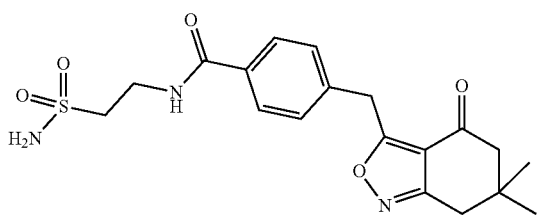 [SMILES: CC1(C)CC(=O)c2c(noc2Cc2ccc(C(=O)NCCS(N)(=O)=O)cc2)C1] | 54 |
| 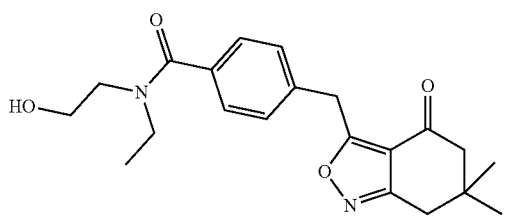 [SMILES: CCN(CCO)C(=O)c1ccc(Cc2onc3c2C(=O)CC(C)(C)C3)cc1] | 55 |
| 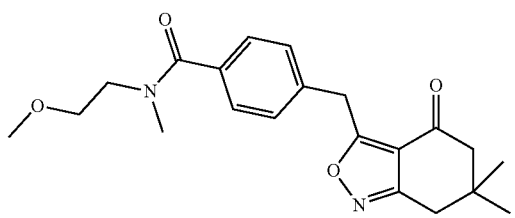 | 56 |
| 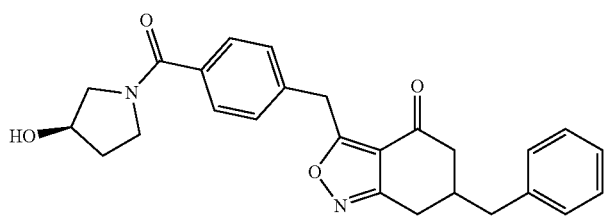 [SMILES: O=C1CC(Cc2ccccc2)Cc2noc(Cc3ccc(C(=O)N4CC[C@@H](O)C4)cc3)c21] | 57 |

-continued
| | |
|---|---|
| 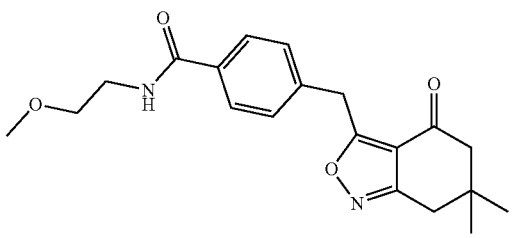 | 58 |
| 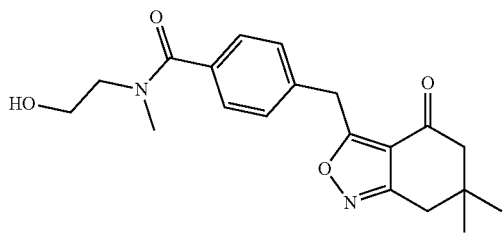 | 59 |
| 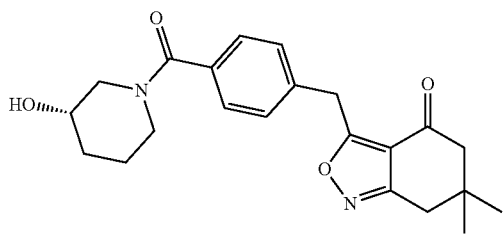 [SMILES: CC1(C)CC(=O)c2c(noc2Cc2ccc(C(=O)N3CCC[C@H](O)C3)cc2)C1] | 60 |
| 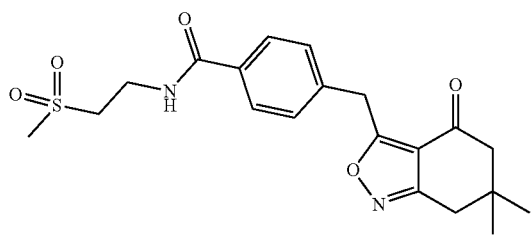 [SMILES: CC1(C)CC(=O)c2c(noc2Cc2ccc(C(=O)NCCS(C)(=O)=O)cc2)C1] | 61 |
| 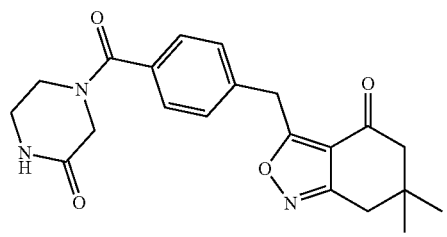 [SMILES: CC1(C)CC(=O)c2c(noc2Cc2ccc(C(=O)N3CCNC(=O)C3)cc2)C1] | 62 |
| 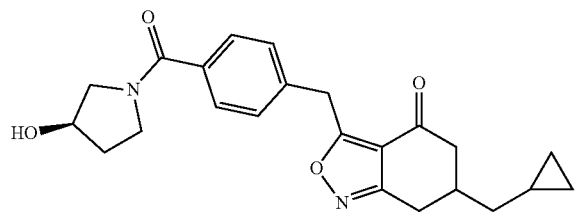 [SMILES: O=C1CC(CC2CC2)Cc2noc(Cc3ccc(C(=O)N4CC[C@@H](O)C4)cc3)c21] | 63 |

| | |
|---|---|
| 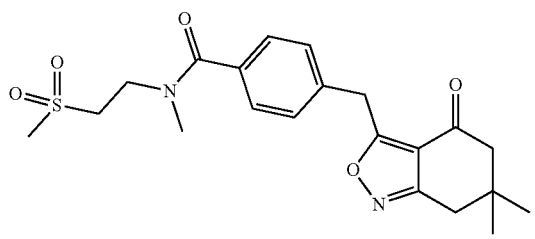 [SMILES: CN(CCS(C)(=O)=O)C(=O)c1ccc(Cc2onc3c2C(=O)CC(C)(C)C3)cc1] | 64 |
| 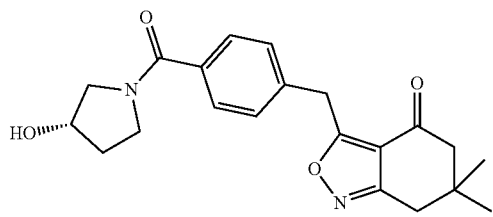 [SMILES: CC1(C)CC(=O)c2c(noc2Cc2ccc(C(=O)N3CC[C@H](O)C3)cc2)C1] | 65 |
| 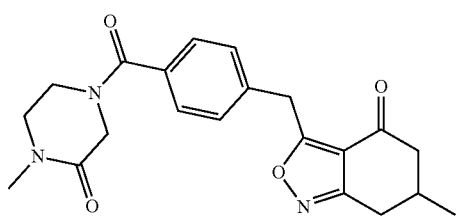 | 66 |
| 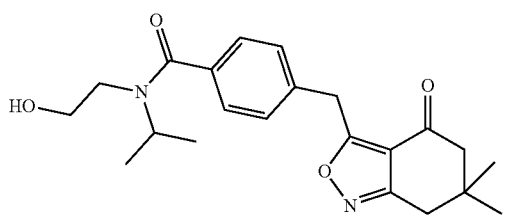 [SMILES: CC(C)N(CCO)C(=O)c1ccc(Cc2onc3c2C(=O)CC(C)(C)C3)cc1] | 67 |
| 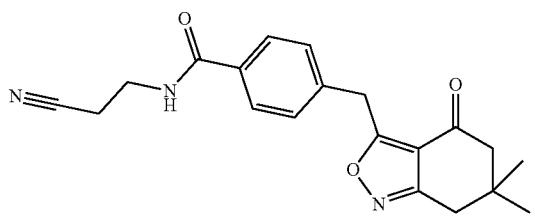 [SMILES: CC1(C)CC(=O)c2c(noc2Cc2ccc(C(=O)NCCC#N)cc2)C1] | 68 |
| 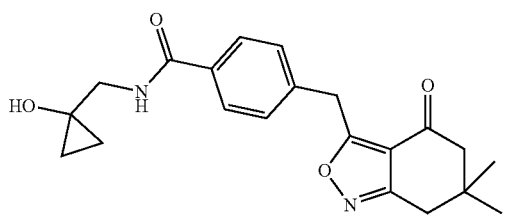 [SMILES: CC1(C)CC(=O)c2c(noc2Cc2ccc(C(=O)NCC3(O)CC3)cc2)C1] | 69 |
| 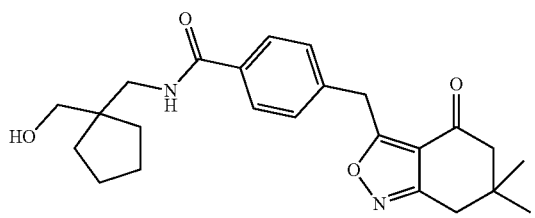 [SMILES: CC1(C)CC(=O)c2c(noc2Cc2ccc(C(=O)NCC3(CO)CCCC3)cc2)C1] | 70 |

-continued
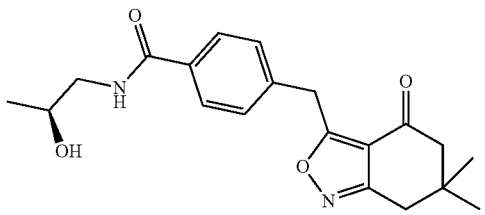 [SMILES: C[C@H](O)CNC(=O)c1ccc(Cc2onc3c2C(=O)CC(C)(C)C3)cc1]
71
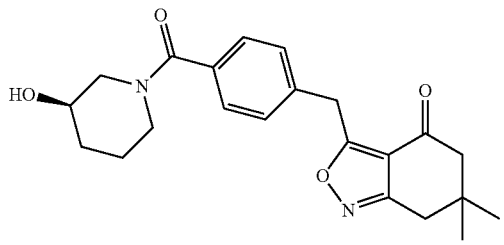 [SMILES: CC1(C)CC(=O)c2c(noc2Cc2ccc(C(=O)N3CCC[C@@H](O)C3)cc2)C1]
72
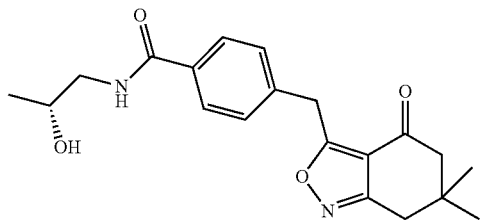 [SMILES: C[C@@H](O)CNC(=O)c1ccc(Cc2onc3c2C(=O)CC(C)(C)C3)cc1]
73
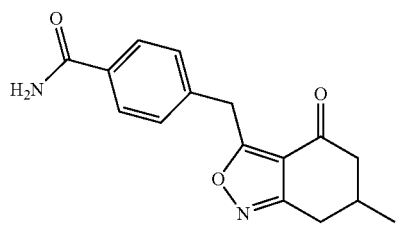 [SMILES: CC1CC(=O)c2c(noc2Cc2ccc(C(N)=O)cc2)C1]
74
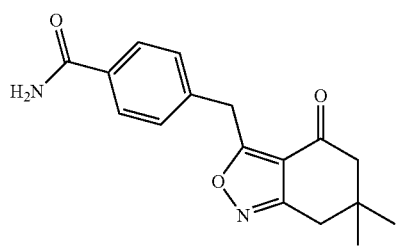 [SMILES: CC1(C)CC(=O)c2c(noc2Cc2ccc(C(N)=O)cc2)C1]
75
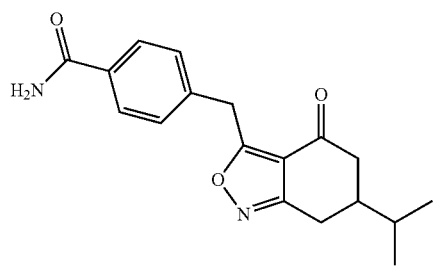 [SMILES: CC(C)C1CC(=O)c2c(noc2Cc2ccc(C(N)=O)cc2)C1]
76

-continued
| | |
|---|---|
| 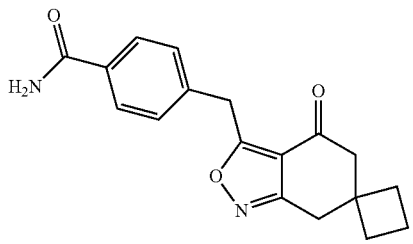 [SMILES: NC(=O)c1ccc(Cc2onc3c2C(=O)CC2(CCC2)C3)cc1] | 77 |
| 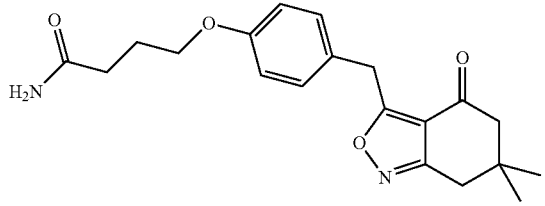 [SMILES: CC1(C)CC(=O)c2c(noc2Cc2ccc(OCCCC(N)=O)cc2)C1] | 78 |
| 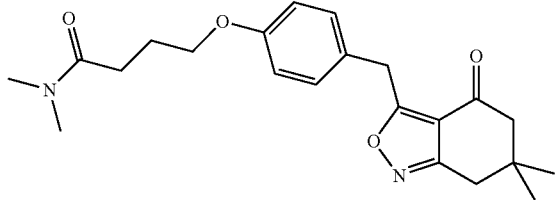 | 79 |
| 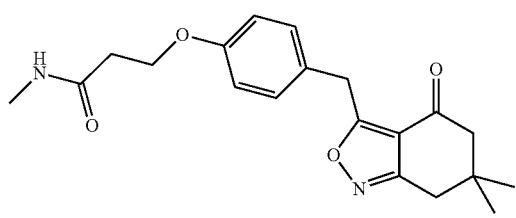 | 80 |
| 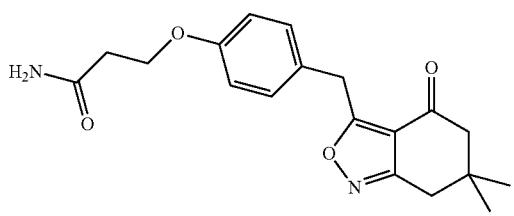 [SMILES: CC1(C)CC(=O)c2c(noc2Cc2ccc(OCCC(N)=O)cc2)C1] | 81 |
| 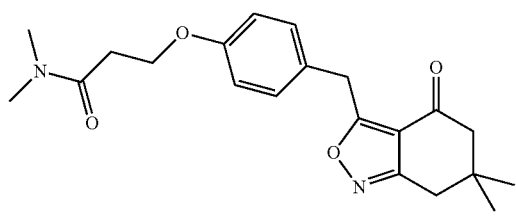 | 82 |
| 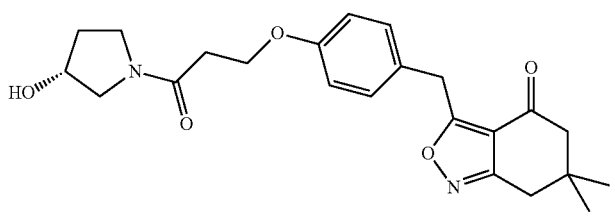 [SMILES: CC1(C)CC(=O)c2c(noc2Cc2ccc(OCCC(=O)N3CC[C@@H](O)C3)cc2)C1] | 83 |

| | |
|---|---|
| 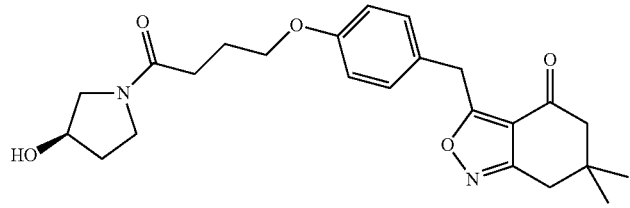 [SMILES: CC1(C)CC(=O)c2c(noc2Cc2ccc(OCCCC(=O)N3CC[C@@H](O)C3)cc2)C1] | 84 |
| 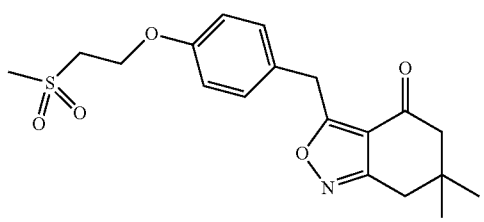 | 85 |
| 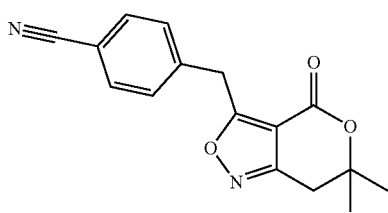 [SMILES: CC1(C)Cc2noc(Cc3ccc(C#N)cc3)c2C(=O)O1] | 87 |
| 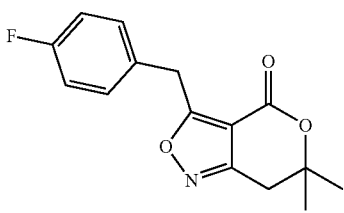 [SMILES: CC1(C)Cc2noc(Cc3ccc(F)cc3)c2C(=O)O1] | 88 |
| 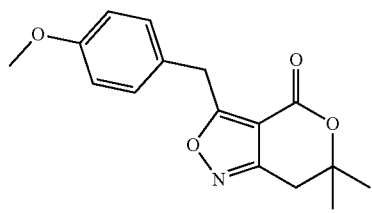 | 89 |
| 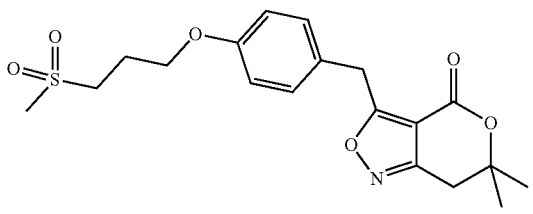 [SMILES: CC1(C)Cc2noc(Cc3ccc(OCCCS(C)(=O)=O)cc3)c2C(=O)O1] | 90 |
| 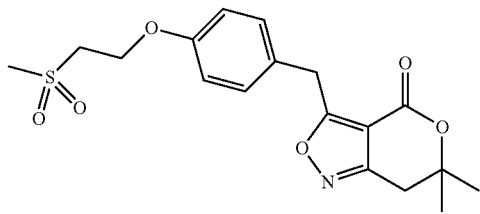 | 91 |

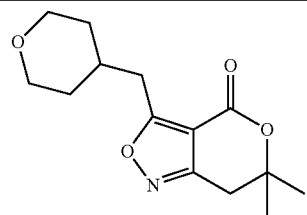

92

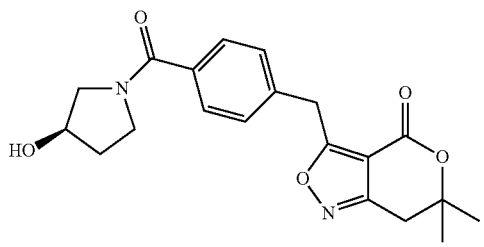 [SMILES: CC1(C)Cc2noc(Cc3ccc(C(=O)N4CC[C@@H](O)C4)cc3)c2C(=O)O1]

93

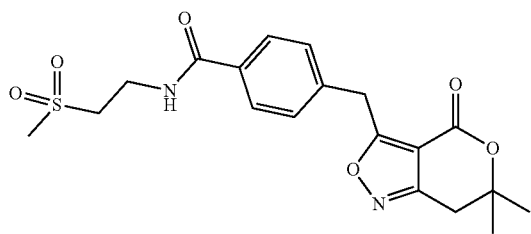 [SMILES: CC1(C)Cc2noc(Cc3ccc(C(=O)NCCS(C)(=O)=O)cc3)c2C(=O)O1]

94

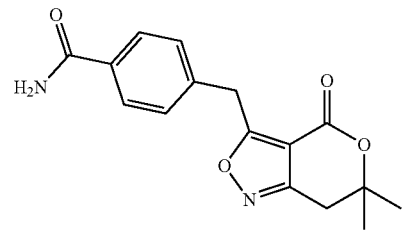 [SMILES: CC1(C)Cc2noc(Cc3ccc(C(N)=O)cc3)c2C(=O)O1]

95

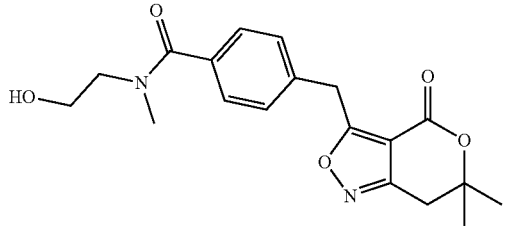 [SMILES: CN(CCO)C(=O)c1ccc(Cc2onc3c2C(=O)OC(C)(C)C3)cc1]

96

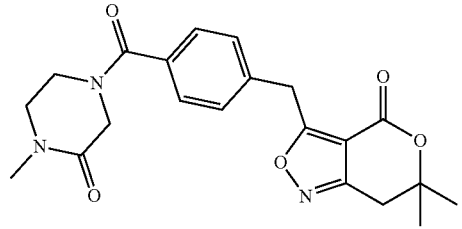

97 or a pharmaceutically acceptable salt thereof.

7. The compound according to claim 6 selected from the group consisting of compound numbers 9, 13, 15-17, 23, 25, 27, 29, 39, 46, 54, 59, 61, 65, 75, 90, 93 and 94 or a pharmaceutically acceptable salt thereof.

8. A pharmaceutical composition comprising a compound according to claim 1 or a pharmaceutically acceptable salt thereof and a pharmaceutically acceptable carrier or adjuvant.

9. A method of treating a disease or disorder that can be alleviated by inhibition of aldosterone synthase selected from diabetic nephropathy, glomerulosclerosis, glomerulonephritis, IGA nephropathy, nephritic syndrome, focal segmental glomerulosclerosis (FSGS), hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis, cardiovascular morbidity associated with primary or secondary hyperaldosteronism, adrenal hyperplasia and primary or secondary hyperaldosteronism, comprising administering a therapeutically effective amount of a compound according to claim 1, or a pharmaceutically acceptable salt thereof, to a patient in need thereof.

10. The method according to claim 9, wherein the disease or disorder is selected from diabetic nephropathy, glomerulosclerosis, glomerulonephritis, IGA nephropathy, nephritic syndrome and focal segmental glomerulosclerosis.

11. The method according to claim 9, wherein the disease is diabetic nephropathy.

\* \* \* \* \*